US006355473B1

(12) United States Patent
Ostanin et al.

(10) Patent No.: US 6,355,473 B1
(45) Date of Patent: Mar. 12, 2002

(54) YEAST CELLS HAVING MUTATIONS IN STP22 AND USES THEREFOR

(75) Inventors: Kirill Ostanin, Shrub Oak; Lauren Silverman, Ossining, both of NY (US)

(73) Assignee: Cadus Pharmaceutical Corp., Tarrytown, NY (US)

( * ) Notice: Subject to any disclaimer, the term of this patent is extended or adjusted under 35 U.S.C. 154(b) by 0 days.

(21) Appl. No.: 09/305,923

(22) Filed: May 5, 1999

Related U.S. Application Data

(60) Provisional application No. 60/084,420, filed on May 6, 1998.

(51) Int. Cl.$^7$ .......................... C12N 1/14; G01N 33/566; C07H 21/04; C07K 1/00
(52) U.S. Cl. ............................ 435/254.21; 435/254.11; 435/7.31; 435/69.1; 435/7.1; 436/501; 536/231; 530/350
(58) Field of Search .......................... 435/7.1, 254.11, 435/254.2, 254.21, 320.7, 69.1, 7.2, 7.31; 530/350; 536/23.4, 23.1; 436/501

(56) References Cited

U.S. PATENT DOCUMENTS

| 4,418,149 A | 11/1983 | Ptashne et al. .............. 435/253 |
| 4,833,080 A | 5/1989 | Brent et al. ............... 435/172.3 |
| 4,948,874 A | 8/1990 | Kronvall et al. ............. 350/350 |
| 5,096,815 A | 3/1992 | Ladner et al. .............. 435/69.1 |
| 5,283,173 A | 2/1994 | Fields et al. .................... 435/6 |
| 5,401,629 A | 3/1995 | Harpold et al. ................. 435/6 |
| 5,436,128 A | 7/1995 | Harpold et al. ................. 435/6 |
| 5,468,614 A | 11/1995 | Fields et al. .................... 435/6 |
| 5,482,835 A * | 1/1996 | King et al. ...................... 435/6 |
| 5,580,736 A | 12/1996 | Brent et al. ...................... 435/6 |
| 5,691,188 A | 11/1997 | Pausch et al. ............. 435/225.1 |
| 5,703,220 A * | 12/1997 | Yamada et al. ............. 536/23.5 |
| 5,739,029 A | 4/1998 | King et al. ............. 435/254.21 |
| 5,789,184 A | 8/1998 | Fowlkes et al. ............ 435/7.31 |
| 5,846,819 A * | 12/1998 | Paush et al. .............. 435/320.1 |
| 5,876,951 A * | 3/1999 | Fowlkes et al. ............ 435/7.31 |

FOREIGN PATENT DOCUMENTS

| EP | 568925 | 11/1993 |
| WO | WO 88/10308 | 12/1988 |
| WO | WO 91/12273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |

OTHER PUBLICATIONS

Corness et al FEBS Lett, 321(279–284)Apr. 1993.*
Mollereau et al. FEBS Lett. 341(33–38)1994.*
Hitzeman et al Meth. Enzymology 185(421–440)1990.*
Price, et al., Mol. Cell. Biol. 15:11(6188–6195)1995.*
Cartwright, et al Mol. Cell. Biol. 11:5(2620–2628)1991.*
Chen et al. P.N.A.S. 90(8967–8971)Oct. 1993.*
Akada, R. et al. "Genetic Relationships Between the G Protein βγ Complex, Ste5p, Ste20p and Cdc42p: Investigation of Effector Roles in the Yeast Pheromone Response Pathway," *Genetics* 143:103–117 (1996).
Alison, Malcolm R. et al. "Growth factors and growth factor receptors," *Brit. J. of Hosp. Med.* 49(11):774–88 (1993).
Altieri, Dario C. "Proteases and protease receptors in modulation of leukocyte effector functions," *J. of Leukocyte Biol.* 58:120–27 (1995).
Artemyev, Nikolai O. et al. "Sites of Interaction between Rod G–Protein α–Subunit and cGMP–phosphodiesterase γ–Subunit," *J. Biol. Chem.* 267(35):25067–72 (1992).
Awramik, S. M. "New fossil finds in old rocks," *Nature* 319:446–47 (1986).
Belka, C. et al. "The role of tyrosine kinases and their substrates in signal transmission of hematopoietic growth factors: a short review," *Leukemia* 9:754–61 (1995).
Bender, Alan and Sprague, George F. Jr. "Pheromones and Pheromone Receptors Are the Primary Determinants of Mating Specificity in the Yeast *Saccharomyces cerevisiae*," *Genetics* 121:463–76 (1989).
Birnbaumer, Lutz "Transduction of receptor signal into modulation of effector activity by G proteins: the first 20 years or so . . . " *FASEB Journal* 4:3178–88 (1990).
Blinder, Dmitry et al. "Constitutive Mutants in the Yeast Pheromone Response: Ordered function of the Gene Products," *Cell* 56:479–486 (1989).
Brill, Julie A. et al. "A Role for Autophosphorylation Revealed by Activated Alleles of FUS3, the Yeast MAP Kinase Homolog," *Molecular Biology of the Cell* 5:297–312 (1994).
Burack, W. Richard et al. "The Activating Dual Phosphorylation of MAPK by MEK Is Nonprocessive," *Biochemistry* 36(20):5929–5933 (1997).
Cartwright, C.P. et al., "In vivo topological analysis of Ste2, a yeast plasma membrane protein, by using beta–lactamase gene fusions," *Mol. Cell. Biol.* 11(5):2620–8 (1991).
Cavallini, Bruno et al. "A yeast activity can substitute for the HeLa Cell TATA box factor," *Nature* 334:77–80 (1988).
Chambers, D. A. et al. "Neuroimmune Modulation: Signal Transduction and Catecholamines," *Neurochem. Int.* 22(2):95–110 (1993).

(List continued on next page.)

*Primary Examiner*—Yvonne Eyler
*Assistant Examiner*—Michael Brannock
(74) *Attorney, Agent, or Firm*—Lahive & Cockfield, LLP; Peter C. Lauro, Esq.; Giulio A. DeConti, Esq.

(57) ABSTRACT

The invention provides yeast cells which comprise a mutation in an endogenous yeast stp22 gene and which express a heterologous G protein coupled receptor. The instant yeast cells display enhanced sensitivity to ligand induced stimulation of heterologous G protein coupled receptors and, therefore, show improved properties in drug screening assays.

23 Claims, No Drawings

OTHER PUBLICATIONS

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1):11–20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999–1011 (1990).

Chen, R. et al., "Expression cloning of a human corticotropin–releasing–factor receptor," *Proc Natl Acad Sci U S A.* 90(19):8967–71 (1993).

Chien, Cheng–Ting, et al. "The two–hybrid system: A method to identify and clone genes for proteins that interact with a protein of interest," *Proc. Natl. Acad. Sci. USA* 88:9578–82 (1991).

Clark, Karen L. et al. "Interactions among the Subunits of the G–protein Involved in *Saccharomyces cerevisiae* Mating," *Molecular and Cellular Biol.* 13(1):1–8 (1993).

Cole, Gary M. et al. "Stoichiometry of G Protein Subunits: Affects the *Saccharomyces cerevisiae* Mating Pheromone Signal Transduction Pathway," *Molecular and Cellular Biology* 10(2):510–517 (1990).

Coleman, David E. et al. "Structures of Active Conformation of $G_{i\alpha1}$ and the Mechanism of GTP Hydrolysis," *Science* 265:1405–12 (1994).

Conklin, Bruce R. et al. "Substitution of three amino acids switches receptor specificity of $G_{q\alpha}$ to that of $G_{i\alpha}$," *Nature* 363:274–76 (1993).

Corness, J.D. et al., "A human somatostatin receptor (SSTR3), located on chromosome 22, displays preferential affinity for somatostatin–14 like peptides," *FEBS Lett.* 321(2–3):279–84 (1993).

Cwirla, Steven E. et al. "Peptides on phage: A vast library of peptides for identifying ligands," *Proc. Natl. Acad. Sci. USA* 87:6378–82 (1990).

Devlin, James J. et al. "Random Peptide Libraries: A Source of Specific Protein Binding Molecules," *Science* 249:404–6 (1990).

Dietzel, Christine and Kurjan, Janet "The Yeast SCG1 Gene: A Gα–like Protein Implicated in the α– and α–Factor Response Pathway," *Cell* 50:1001–10 (1987).

Dmochowska, Aleksandra et al. "Yeast KEX1 Gene Encodes a Putative Protease with a Carboxypeptidase B–like Function Involved in Killer Toxin and α–Factor Precursor Processing," *Cell* 50:573–84 (1987).

Dolan, J. W. et al. "Overproduction of the yeast STE12 protein leads to constitutive transcriptional induction," *Genes & Development* 4(4):492–502 (1990).

Dubois, Patrice M. et al. "Role of the transmembrane and cytoplasmic domains of surface IgM in endocytosis and signal transduction," *Eur. J. Immunol.* 22:851–57 (1992).

Erickson, Deborah "Intercepted Messages: New biotechnology drugs target intracellular communication," *Scientific American* 267(5):122–23 (1992).

Etienne, Gilles et al. "A Screening Method for Antifungal Substances Using *Saccharomyces cerevisiae* Strains Resistant to Polyene Macrolides," *J. of Antibiotics* 43(2):199–206 (1990).

Fasullo, Michael T. and Davis, Ronald W. "Direction of Chromosome Rearrangements in *Saccharomyces cerevisiae* by Use of his3 Recombination Substrates," *Molecular and Cellular Biol.* 8(10):4370–80 (1988).

Ferrell, James E. Jr. et al. "The Biochemical Basis of an All–or–None Cell Fate Switch in Xenopus Oocytes," *Science* 280:895–898 (1998).

Ferrell, James E. Jr. "Tripping the switch fantastic: how a protein kinase cascade can convert graded inputs into switch–like outputs," *Trends In Biochem. Sci.* 21(12):460–6 (1996).

Fields, Stanley and Song Ok–kyu "A novel genetic system to detect protein–protein interactions," *Nature* 340:245–46 (1989).

Franke, Arthur E. et al. "Human C5a Anaphylatoxin: Gene Synthesis, Expression, and Recovery of Biologically Active Material from *Escherichia coli,*" *Methods in Enzymology* 162:653–68 (1988).

Funaro, Ana et al. "Human CD38 is associated to distinct molecules which mediate transmembrane signaling in different lineages," *Eur. J. Immunol.* 23:2407–11 (1993).

Gallego, Carme et al. "Myristoylation of the $G_{\alpha i2}$ polypeptide, a G protein α subunit, is required for its signaling and transformation functions," *Proc. Natl. Acad. Sci. USA* 89:9695–99 (1992).

Garritsen, Anja et al. "The N–Terminal coiled–coil domain of α is essential for γ association: A Model for G–Protein βγ subunit interaction," *Proc. Natl. Acad. Sci. USA* 90:7706–10 (1993).

Gerard, Norma P. and Gerard, Craig "Construction and Expression of a Novel Recombinant Anaphylatoxin, C5a–N19, a Probe for the Human C5a Receptor," *Biochemistry* 29(39):9274–81 (1990).

Gordon, J. "B–cell signaling via the C–type lectins CD23 and CD72," *Immunology Today* 15(9):411–17 (1994).

Graf, Rolf et al. "A Truncated Recombinant α Subunit of $G_{i3}$ with a Reduced Affinity for βγ Dimers and Altered Guanosine 5'–3–O–(Thio)triphosphate Binding," *J. of Biol. Chem.* 267(34):24307–14 (1992).

Gros, Philippe et al. "Mammalian Multidrug Resistance Gene: Complete cDNA Sequence Indicates Strong Homology to Bacterial Transport Proteins," *Cell* 47:371–80 (1986).

Gyuris, Jenö et al. "Cdi1, A Human G1 and S Phase Protein Phosphatase That Associates with Cdk2," *Cell* 75:791–803 (1993).

Hagen, David C. et al. "Evidence the yeast STE3 gene encodes a receptor for the peptide pheromone a factor: Gene sequence and implications for the structure of the presumed receptor," *Proc. Natl. Acad. Sci. USA* 83:1418–22 (1986).

Harbury, Pehr B. et al. "A Switch Between Two–, Three– and Four–Stranded Coiled Coils in GCN4 Leucine Zipper Mutants," *Science* 262:1401–07 (1993).

Hartwell, Leland H. "Mutants of *Saccharomyces cerevisiae* Unresponsive to Cell Division Control by Polypeptide Mating Hormone," *J. Cell Biol.* 85:811–22 (1980).

Hasson, M.S. et al. "Mutational Activation of the STE5 Gene Product Bypasses the Requirement for G Protein β and γ Subunits in the Yeast Pheromone Response Pathway," *Molecular and Cellular Biology* 14(2):1054–1065 (1994).

He, Bin et al. "RAM2, an essential gene of yeast, and RAM1 encode the two polypeptide components of the farnesyltransferase that prenylates a–factor and Ras proteins," *Proc. Natl. Acad. Sci. USA* 88:11373–77 (1991).

Hiltunen, J. Kalervo et al. "Peroxisomal Multifunctional β–Oxidation Protein of *Saccharomyces cerevisiae,*" *J. of Biol. Chem.* 267(10):6646–6653 (1992).

Hitzeman, R.A. et al., "Use of heterologous and homologous signal sequences for secretion of heterologous proteins from yeast," *Methods Enzymol.* 185:421–40 (1990).

Hrycyna, Christine A. et al. "The *Saccharomyces cerevisiae* STE14 gene encodes a methyltransferase that mediates C–terminal methylation of a–factor and RAS Proteins," *The EMBO J.* 10(1):1699–1709 (1991).

Huang, Chi–Ying F. et al. "Ultrasensitivity in the mitogen–activated protein kinase cascade," *Proc. Natl. Acad. Sci. USA* 93:10078–10083 (1996).

Hughes, David A. et al. "Complementation of byr1 in fission yeast by mammalian MAP kinase kinase requires coexpression of Raf kinase," *Nature* 364:349–52 (1993).

Inouye, Carla et al. "Ste5 RING–H2 Domain: Role in Ste4–Promoted Oligomerization for Yeast Pheromone Signaling," *Science* 278:103–106 (1997).

Jabbar, M. Abdul et al. "Influenza Viral (A/WSN/33) hemagglutinin in expressed and glycosylated in the yeast *Saccharomyces cerevisiae*," *Proc. Natl. Acad. Sci. USA* 82:2019–23 (1985).

Jakobs, K. H. et al. "Dual regulation of adenylate cyclase. A signal transduction mechanism of membrane receptors," *Basic Res. Cardiol.* 81:1–9 (1986).

Journot, Laurent et al. "Amino Acids 367–376 of the $G_S$ α subunit induce membrane association when fused to soluble amino–terminal deleted $G_{i1}$ a subunit," *Proc. Natl. Acad. Sci. USA* 88:10054–58 (1991).

Julius, David et al. "Glycosylation and Processing of Prepro–α–Factor through the Yeast Secretory Pathway," *Cell* 36:309–18 (1984).

Julius, David et al. "Isolation of the Putative Structural Gene for the Lysine–Arginine–Cleaving Endopeptidase Required for Processing of Yeast Prepro–α–Factor through the Yeast Secretory Pathway," *Cell* 36:309–18 (1984).

Julius, David et al. "Yeast α Processed from a Larger Precursor Polypeptide: The Essential Role of a Membrane–Bound Dipeptidyl Aminopeptidase," *Cell* 32:839–52 (1983).

Kaiser, Chris A. et al. "Many Random Sequences Functionally Replace the Secretion Signal Sequence of Yeast Invertase," *Science* 235:312–17 (1987).

Kang, Yoon–Se et al. "Effects of expression of mammalian Gα and hybrid mammalian–yeast Gα proteins on the yeast pheromone response signal transduction pathway," *Molecular and Cellular Biology* 10(6):2582–2590 (1990) verify page numbers!!

King, Klin et al. "Control of Yeast Mating Signal Transduction by a Mammalian $\beta_2$–Adrenergic Receptor and $G_S$ α Subunit," *Science* 250:121–23 (1990).

Kingsman, S.M. et al. "The production of mammalian protein in *Saccharomyces cerevisiae*," *Tibtech* 5:53–57 (1987).

Koff, Andrew et al. "Human Cyclin E, a New Cyclin That Interacts with Two Members of the CDC2 Gene Family," *Cell* 66:1217–28 (1991).

Kosugi, Shinji et al. "Characterization of heterogeneous mutations causing constitutive activation of the luteinizing hormone receptor in familial male precocious puberty," *Human Molecular Genetics* 4(2):183–88 (1995).

Kramer, R. A. et al. "HTLV–III gag Protein Is Processed in Yeast Cells by the Virus pol–Protease," *Science* 231:1580–85 (1986).

Kuchler, Karl and Thorner, Jeremy "Functional expression of human mdr1 in the yeast *Saccharomyces cerevisiae*," *Proc. Natl. Acad. Sci. USA* 89:2302–06 (1992).

Kuchler, Karl et al. "*Saccharomyces cerevisiae* STE6 gene product: a novel pathway for protein export in eukaryotic cells," *The EMBO J.* 8(13):3973–84 (1989).

Kurjan, Janet "α–Factor Structural Gene Mutations in *Saccharomyces cerevisiae:* Effects on α–Factor Production and Mating," *Molecular and Cellular Biol.* 5(4):787–96 (1985).

Kurjan, Janet and Herskowitz "Structure of a Yeast Pheromone Gene (MFα): A Putative α–Factor Precursor Contains Four Random Copies of Mature α–Factor," *Cell* 30:933–43 (1982).

Lambright, David G. et al. "Structural determinants for activation of the α–subunit of a heterotrimeric G protein," *Nature* 369:621–28 (1994).

Leberer, Ekkehard et al. "Dominant–negative mutants of a yeast G–protein β subunit identify two functional regions involved in pheromone signaling," *The EMBO J.* 11(13):4805–13 (1992).

Lee, Ethan et al. The G22A Mutant of $G_{S\alpha}$ Highlights the Requirement for Dissociation of G Protein Subunits, *J. Biol. Chem.* 267(2):1212–18 (1992).

Lemire, Bernard D. et al. "The Mitochondrial Targeting Function of Randomly Generated Peptide Sequences Correlates with Predicted Helical Amphiphilicity," *J. Biol. Chem.* 264(34):20206–12 (1989).

Lew, Daniel J. et al. "Isolation of Three Novel Cyclins by Rescue of G1 Cyclin (Cln) Function in Yeast," *Cell* 66:1197–1206 (1991).

Linder, Maurine E. and Gilman, Alfred G. "G Proteins," *Scientific American* 267(1):56–65 (1992).

Linder, Maurine E. et al. "Lipid Modifications of G Protein Subunits: Myristoylation of $G_{O\alpha}$ Increases its Affinity for βγ," *J. Biol. Chem.* 266(7):4654–59 (1991).

Lolait et al., "Extrapituitary expression of the rat V1b vasopressin receptor gene," *PNAS USA* 92:6783–6787 (1995).

Lupas, Andrei N. et al. "Do G protein subunits associate via a three–stranded coiled coil?" *FEBS* 314(2):105–08 (1992).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273–88 (1974).

Marengere, Luc E.M. and Pawson, Tony "Structure and function of SH2 domains," *J. Cell Science* Suppl. 18:97–104 (1994).

Markby, David W. et al. "Separate GTP Binding and GTPase Activating Domains of a Gα Subunit," *Science* 262:1895–1901 (1993).

Michaelis, Susan and Herskowitz, Ira "The α–Factor Pheromone of *Saccharomyces cerevisiae* is Essential for Mating," *Molecular and Cellular Biol.* 8(3):1309–18 (1988).

Milano, C.A. et al. "Enhanced Myocardial Function in Transgenic Mice Overexpressing the $\beta_2$–Adrenergic Receptor," *Science* 264:582–86 (1994).

Mollereau, C. et al., "ORL1, a novel member of the opioid receptor family. Cloning, functional expression and localization," *FEBS Lett.* 341(1):33–8 (1994).

Mumby, Susanne M. et al. "G–Protein α–subunit expression, myristoylation, and membrane association in COS cells," *Proc. Natl. Acad. Sci. USA* 87:728–32 (1990).

Murphy, A.J.M. et al. "Autocrine Stimulation of Yeast through Human G–Coupled Receptors," *J. Cell Biochem.* 18B:224 (1994).

Nakafuku, Masato et al. "Occurrence in *Saccharomyces cerevisiae* of a gene homologous to the cDNA coding for the α–subunit of mammalian G proteins," *Proc. Natl. Acad. Sci. USA* 84:2140–44 (1987).

Nakayama, N. et al. "Common signal transduction system shared by STE2 and STE3 in haploid cells of *Saccharomyces cerevisiae:* autocrine cell–cycle arrest results from forced expression STE2," *The EMBO J.* 6(1):249–254 (1987).

Neer, Eva J. et al. "The Amino Terminus of a G Protein α Subunits Is Required for Interaction with βγ," *J. Biol. Chem.* 263(18):8996–9000 (1988).

Noel, Joseph P. et al. "The 2.2 Å crystal structure of transducin–α complexed with GTP–γ–S," *Nature* 366:654–63 (1993).

Noelle, Randolph J. et al. "CD40 and its ligand, an essential ligand–receptor pair for thymus–dependent B–cell activation," *Immunol. Today* 13(11):431–33 (1992).

Nomoto, Satoshi et al. "Regulation of the yeast pheromone response pathway by G protein subunits," *The EMBO J.* 9(3):691–696 (1990).

Nye, Jeffrey S. and Kopan, Raphael "Vertebrate ligands for Notch," *Current Biology* 5(9):966–69 (1995).

Oeda, Kenji et al. "Expression of Rat Liver Cytochrome P–450MC cDNA in *Saccharomyces cerevisiae,*" *DNA* 4(3):203–10 (1985).

Ogden, Jill E. et al. "Efficient Expression of the *Saccharomyces cerevisiae* PGK Gene Depends on an Upstream Activation Sequence but Does Not Require TATA Sequences," *Molecular and Cellular Biol.* 6(12):4335–43 (1986).

Price, L.A. et al., "Functional coupling of a mammalian somatostatin receptor to the yeast pheromone response pathway," *Mol Cell Biol.* 15(11):6188–95 (1995).

Pronin, Alexey N. and Gautam, Narasimhan "Interaction between G–Protein β and γ subunit types is selective," *Proc. Natl. Acad. Sci. USA* 89:6220–24 (1992).

Ramer, Sandra W. and Davis, Ronald W. "A dominant truncation allele identifies a gene, STE20, that encodes a putative protein kinase necessary for mating in *Saccharomyces cerevisiae,*" *Proc. Natl. Acad. Sci. USA* 90:452–456 (1993).

Rarick, Helen M. et al. "A Site on Rod G Protein α Subunit That Mediates Effector Activation," *Science* 256:1031–33 (1992).

Raymond, Martine et al. "Functional Complementation of Yeast ste6 by a Mammalian Multidrug Resistence mdr Gene," *Science* 256:232–34 (1992).

Reed, Randall R. "G Protein Diversity and the Regulation of Signaling Pathways," *The New Biologist* 2(11):957–60 (1990).

Schafer, William R. et al. "Enzymatic Coupling of Cholesterol Intermediates to a Mating Pheromone Precursor and to the Ras Protein," *Science* 249:1133–39 (1990).

Schafer, William R. et al. "Genetic and Pharmacological Suppression of Oncogenic Mutations in RAS Genes of Yeast and Humans," *Science* 245:379–85 (1989).

Schärer, E. and Iggo, R. "Mammalian p53 can function as a transcription factor in yeast," *Nucleic Acids Research* 20(7):1539–45 (1992).

Scott, Jamie K. and Smith, George P. "Searching for Peptide Ligands with an Epitope Library," *Science* 249:386–90 (1990).

Sikorski, Robert S. and Hieter, Philip "A System of Shuttle Vectors and Yeast Host Strains Designed for Efficient Manipulation of DNA in *Saccharomyces cerevisiae,*" *Genetics* 122:19–27 (1989).

Singh, Arjun et al. "*Saccharomyces cerevisiae* contains two discrete genes coding for the α–factor pheromone," *Nucleic Acids Research* 11(12):4049–63 (1983).

Slepák, Vladlen Z. et al. "Mutational Analysis of G Protein α Subunit $G_{0\alpha}$ Expressed in *Escherichia coli,*" *J. Biol. Chem.* 268(2):1414–23 (1993).

Spiegel, Allen M. et al. "The G Protein connection: molecular basis of membrane association," *TIBS* 16:338–41 (1991).

Steube, Klaus et al. "α–Factor–leader–directed secretion of recombinant human–insulin–like growth factor I from *Saccharomyces cerevisiae,*" *Eur. J. Biochem.* 198:651–57 (1991).

Stevenson, Brain J. et al. "Constitutive mutants of the Protein Kinase STE11 Activate the Yeast Pheromone Response Pathway in the Absence of the G Protein," *Genes & Development* 6:1293–1304 (1992).

Strubin, Michel and Struhl, Kevin "Yeast and Human TFIID with Altered DNA–Binding Specificity of TATA Elements," *Cell* 68:721–30 (1992).

Struhl, Kevin "Constitutive and Inducible *Saccharomyces cerevisiae* Promoters: Evidence for Two Distinct Molecular Mechanisms," *Molecular and Cellular Biol.* 6(11):3847–53 (1986).

Struhl, Kevin et al. "High–frequency transformation of yeast: Autonomous replication of hybrid DNA molecules," *Proc. Natl. Acad. Sci. USA* 76(3):1035–39 (1979).

Struhl, Kevin and Hill, David E. "Two Related Regulatory Sequences are Required for Maximal Induction of *Saccharomyces cerevisiae* his3 Transcription," *Molecular and Cellular Biol.* 7(1):104–10 (1987).

Sullivan, Kathleen A. et al., "Identification of receptor contact site involved in receptor–G protein coupling," *Nature* 330:758–60 (1987).

Teem, John L. et al. "Identification of Revertants for the Cystic Fibrosis ΔF508 Mutation Using STE6–CFTR Chimeras in Yeast," *Cell* 73:335–346 (1993).

Thomas, Thomas C. et al. "G–protein $\alpha_o$ subunit: Mutation of conserved cysteines identifies a subunit contact surface and alters GDP affinity," *Proc. Natl. Acad. Sci. USA* 90:10295–99 (1993).

Tyson, John J. et al. "Chemical kinetic theory: understanding cell–cycle regulation," *Trends In Biochem. Sci.* 21:89–96 (1996).

Walker, John E. et al., "Distantly related sequences in the α–and β–subunits of ATP synthase, myosin, kinases and other ATP–requiring enzymes and a common nucleotide binding fold," *The EMBO J.* 1(8):945–51 (1982).

Waters, M. Gerard et al. "Prepro–α–factor Has a Cleavable Signal Sequence," *J. Biol. Chem.* 263(13):6209–14 (1988).

Whiteway, Malcolm S. et al. "Association of the Yeast Pheromone Response G Protein βγ Subunits with the MAP Kinase Scaffold Ste5p," *Science* 269:1572–1575 (1995).

Whiteway, Malcolm et al. "Genetic Identification of Residues Involved in Association of α and β G–Protein Subunits," *Molecular and Cellular Biol.* 14(5):3223–3229 (1994).

Whiteway, Malcolm et al. "The STE4 and STE18 Genes of Yeast Encode Potential β and γ Subunits of the Mating Factor Receptor–Coupled G Protein," *Cell* 56:467–477 (1989).

Xiong, Yue et al. "Human D–Type Cyclin," *Cell* 65:691–99 (1991).

Zervos, Antonis S. et al. "Mxi1, a Protein that Specifically Interacts with Max to Bind Myc–Max Recognition Sites," *Cell* 72:223–32 (1993).

Zhan, Xiao–Li et al. "Differential regulation of FUS3 MAP kinase by tyrosine–specific phosphatases PTP2/PTA3 and dual–specificity phosphatase MSG5 in *Saccharomyces cerevisiae*," *Genes & Development* 11:1690–1702 (1997).

* cited by examiner

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
catgccatgg agcccctctt cc                                          22

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
catgtctaga ttatgcgggc cgcggtacc                                   29

<210> SEQ ID NO 3
<211> LENGTH: 10
<212> TYPE: PRT
<213> ORGANISM: Saccharomyces cerevisiae

<400> SEQUENCE: 3

Leu Leu Leu Leu Gly Ala Gly Glu Ser Gly
 1               5                  10

<210> SEQ ID NO 4
<211> LENGTH: 8
<212> TYPE: PRT
<213> ORGANISM: Saccharomyces cerevisiae

<400> SEQUENCE: 4

Leu Leu Leu Leu Gly Ala Gly Glu
 1               5

<210> SEQ ID NO 5
<211> LENGTH: 9
<212> TYPE: PRT
<213> ORGANISM: Saccharomyces cerevisiae

<400> SEQUENCE: 5

Gly Ser Gly Glu Ser Gly Asp Ser Thr
 1               5

<210> SEQ ID NO 6
<211> LENGTH: 8
<212> TYPE: PRT
<213> ORGANISM: Saccharomyces cerevisiae

<400> SEQUENCE: 6

Gln Ala Arg Lys Leu Gly Ile Gln
 1               5

<210> SEQ ID NO 7
<211> LENGTH: 9
<212> TYPE: PRT
<213> ORGANISM: Saccharomyces cerevisiae

```
<400> SEQUENCE: 7

Leu Ile His Glu Asp Ile Ala Lys Ala
  1               5

<210> SEQ ID NO 8
<211> LENGTH: 5
<212> TYPE: PRT
<213> ORGANISM: Saccharomyces cerevisiae

<400> SEQUENCE: 8

Asp Val Gly Gly Gln
  1               5

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 9
ccagatctgg                                                        10
```

YEAST CELLS HAVING MUTATIONS IN STP22 AND USES THEREFOR

CROSS REFERENCE TO RELATED APPLICATIONS AND INCORPORATION BY REFERENCE

This application claims the benefit of U.S. Provisional Application No. 60/084,420, filed May 6, 1998, which is hereby incorporated by reference in its entirety. All patents, published patent applications and other references cited throughout this specification are hereby incorporated by reference in their entireties.

BACKGROUND OF THE INVENTION

Cell surface receptors are an important class of proteins involved in cellular functioning because they are the primary mediators of cell to cell communication. In particular, G protein coupled receptors (GPCRs) are an important category of cell surface receptors. The medical importance of these receptors is evidenced by the fact that more than 60% of all commercially available prescription drugs work by interacting with known GPCRs.

In their resting state, the G proteins, which consist of alpha ($\alpha$), beta ($\beta$) and gamma ($\gamma$) subunits, are complexed with the nucleotide guanosine diphosphate (GDP) and are in contact with the receptors to which they are coupled. When a hormone or other first messenger binds to receptor, the receptor changes conformation and this alters its interaction with the G protein. This spurs the $\alpha$ subunit to release GDP, and the more abundant nucleotide guanosine triphosphate (GTP) replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct G$\alpha$ subunit forms have been isolated. Most G protein-coupled receptors are comprised of a single protein chain that is threaded through the plasma membrane seven times. Such receptors are often referred to as seven-transmembrane receptors (STRs). More than a hundred different GPCRs have been found, including many distinct receptors that bind the same ligand, and there are likely many more GPCRs awaiting discovery.

The mating factor receptors of yeast cells (STE2 and STE3) span the membrane of the yeast cell seven times and are coupled to yeast G proteins. Heterologous GPCRs can be expressed in yeast cells and can be made to couple to yeast G proteins resulting in the transduction of signals via the endogenous yeast pheromone system signaling pathway which is normally activated by STE2 or STE3. In some cases, such heterologous receptors can be made to couple more effectively to the yeast pheromone system signaling pathway by coexpressing a heterologous G protein $\alpha$ subunit (e.g. U.S. Pat. No. 5,482,835 to King et al), by expressing a chimeric G protein subunit (e.g. WO 94/23025), or by expressing a chimeric G protein coupled receptor (e.g., U.S. Pat. No. 5,576,210 issued to Sledziewski et al.).

The $\beta\gamma$ subunits of the activated G protein stimulate the downstream elements of the pheromone system pathway, including the Ste20p protein kinase, and a set of kinases that are similar to MEK kinase, MEK (MAP kinase kinase), and MAP kinase of mammalian cells and are encoded by the STE11, STE7, and FUS3/KSS1 genes, respectively (Whiteway et al. 1995. Science. 269:1572).

In recent years drug discovery has been advanced by expression of heterologous receptors in living cells. However, due to the complexities inherent in such heterologous expression studies, the development of reliable assays to search for modulators of these receptors has presented particular challenges. For example it is often difficult to obtain sufficient expression of heterologous G protein coupled receptors. The development of new means of optimizing heterologous receptor expression would be would be of tremendous benefit in the development of improved drug screening assays.

SUMMARY OF THE INVENTION

The present invention provides an important advance in drug screening methodologies for identifying modulators of G protein coupled receptors by providing, inter alia, a means by which expression of heterologous G protein coupled receptors in the membrane of yeast host cells is optimized, thereby enhancing signaling via the heterologous receptor.

In one embodiment, the invention pertains to a recombinant yeast cell having an endogenous yeast pheromone system pathway and further having a heterologous G protein coupled receptor which functionally couples to the endogenous yeast pheromone system pathway and a mutation which renders an endogenous yeast Stp22 protein nonfunctional. In a further embodiment, such a yeast cell further comprises a heterologous or chimeric G protein subunit. In yet another embodiment, such a yeast cell also has a reporter gene construct which produces a detectable signal upon stimulation of the yeast pheromone system pathway.

In preferred embodiments, the yeast cell of the present invention are Saccharomyces cells.

In one embodiment, a heterologous G protein coupled receptor (e.g., a mammalian GPCR) is expressed in a yeast cell using a native leader sequence of the heterologous G protein coupled receptor. Alternatively, a heterologous G protein coupled receptor that naturally lacks a leader sequence can be expressed in the yeast cell. Still further, an unrelated leader sequence (i.e., a leader sequence that is heterologous to the GPCR, such as a yeast leader sequence with a mammalian GPCR) can be used to express the heterologous G protein coupled receptor. This unrelated leader sequence can be, for example, added to a heterologous GPCR that does not itself contain a leader sequence, or can replace the native leader sequence of a heterologous GPCR that itself contains a leader sequence, or can be added in tandem to a heterologous GPCR that itself contains a leader sequence (such that the resultant construct contains both the unrelated leader and the native leader). In one embodiment, the heterologous G protein coupled receptor is expressed in the yeast cell using a leader sequence other than an $\alpha$-factor leader sequence.

In a preferred embodiment, the heterologous G protein coupled receptor is a mammalian G protein coupled receptor. In a particularly preferred embodiment, the heterologous G protein coupled receptor is a human G protein coupled receptor.

In a preferred embodiment, the heterologous G protein coupled receptor expressed by a yeast cell is a human nociceptin receptor. In another preferred embodiment, the heterologous G protein coupled receptor is a human melanocortin receptor. In a more preferred embodiment, the human melanocortin receptor is hMCR4 or hMCR5. In yet another preferred embodiment the heterologous G protein coupled receptor is a human somatostatin receptor. In a more preferred embodiment, the human somatostatin receptor is hSSTR2 or hSSTR3. In still another preferred embodiment, the heterologous G protein coupled receptor is a human corticotropin releasing receptor. In a more preferred embodiment, the human corticotropin releasing receptor is hCRFR1 or hCRFR2α.

In another embodiment, the invention pertains to a method of identifying compounds which modulate a G protein coupled receptor, comprising the steps of: a) providing a yeast cell having (i) a heterologous G protein coupled receptor which functionally couples to the yeast pheromone system pathway; and (ii) a mutation which renders an endogenous yeast stp22 protein nonfunctional; b) contacting the yeast cell with a compound; and c) identifying compounds which induce a change in a detectable signal in the yeast cell, wherein said detectable signal indicates that the compound is a modulator of the heterologous G protein coupled receptor.

In a preferred embodiment the yeast cell used for such an assay further comprises a reporter gene construct.

In another preferred embodiment the compounds to be tested in the subject assays are from a library of non-peptidic organic molecules.

DETAILED DESCRIPTION OF THE INVENTION

The present invention provides novel yeast cells and assays utilizing such cells for screening and identifying pharmaceutically effective compounds that specifically modulate the activity of a heterologous G protein coupled receptor (GPCR) expressed in a yeast cell. The subject assays enable rapid screening of large numbers of compounds (e.g., compounds in a library) to identify those which are receptor agonists or antagonists. Compositions of matter, such as novel recombinant yeast cells and novel gene constructs, are also embraced by the present invention. The instant assays provide a convenient format for discovering compounds which can be useful in modulating cellular function, as well as in understanding the pharmacology of compounds that specifically interact with cellular receptors.

The instant invention provides yeast cells, and methods of use therefore, in which expression of a heterologous G protein coupled receptor is increased through use of a yeast host cell having a mutation in a particular gene involved in the control of vacuolar protein transport. More particularly, in the invention is based, at least in part, on the finding that yeast cells which have a mutation in stp22 show more robust signaling upon stimulation of heterologous G protein coupled receptors than yeast cells which do not have such a mutation.

In the practice of the instant invention, standard techniques known in the art can be used. See for example, Sherman. 1991. Methods Enzymol. 194:3; Sherman and Hicks. 1991. Methods Enzymol. 194:21; Sambrook et al. *Molecular Cloning A Laboratory Manual*, 2nd Ed., ed. by Sambrook, Fritsch and Maniatis (Cold Spring Harbor Laboratory Press: 1989 or 1991 edition).

Before further description of the invention, certain terms employed in the specification, examples and appended claims are, for convenience, collected here.

I. Definitions

The term "compound" as used herein (e.g., as in "test compound") is meant to include both exogenously added test compounds and peptides endogenously expressed from a peptide library. For example in certain embodiments, the reagent cell also produces the test compound which is being screened. For instance, the reagent cell can produce, e.g., a test polypeptide, a test nucleic acid and/or a test carbohydrate which is screened for its ability to modulate the heterologous receptor activity. In such embodiments, a culture of such reagent cells will collectively provide a library of potential effector molecules and those members of the library which either agonize or antagonize the receptor function can be selected and identified. Moreover, it will be apparent that the reagent cell can be used to detect agents which transduce a signal via the receptor of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

As used herein, "recombinant cells" include any cells that have been modified by the introduction of heterologous DNA. Exemplary control cells include cells that are substantially identical to the recombinant cells, but do not express one or more of the proteins encoded by the heterologous DNA, e.g., do not include or express a reporter gene construct, receptor or test polypeptide, or express a different heterologous DNA (e.g., a cell that expresses a different GPCR that couples to the same G protein as that of the GPCR whose activity is being examined).

As used herein, "heterologous DNA" or "heterologous nucleic acid" includes DNA that does not occur naturally as part of the genome in which it is present or which is found in a location or locations in the genome that differs from that in which it occurs in nature or which is operatively linked to DNA to which it is not normally linked in nature (i.e., a gene that has been operatively linked to a heterologous promoter). Heterologous DNA is not naturally occurring in that position or is not endogenous to the cell into which it is introduced, but has been obtained from another cell. Heterologous DNA can be from the same species or from a different species. In some embodiments, it is mammalian, e.g., human. Any DNA that one of skill in the art would recognize or consider as heterologous or foreign to the cell in which is expressed is herein encompassed by the term heterologous DNA. Examples of heterologous DNA include, but are not limited to, genes which encode proteins that amplify signals transduced via the pheromone response pathway DNA that encodes test polypeptides, receptors, reporter genes, transcriptional and translational regulatory sequences or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, the term "high copy number plasmid" refers to a plasmid which exists in at least 5, or more, copies per cell, and more preferably in at least 10–20 copies per cell. The term "low copy number plasmid" refers to a plasmid which exists in fewer than 5 copies per cell, more preferably 2–3 copies, or less, per cell.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface receptors and modulate the activity of such receptors. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

As used herein, "heterologous G protein receptor" is encoded by heterologous DNA and, upon expression of this heterologous DNA in a recombinant cell, the heterologous receptor is expressed in the recombinant cell. Exemplary GPCRs are described in detail herein.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translationial modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signaling pathway" refers to the components involved in "signal transduction" of a particular signal into a cell. The term "endogenous signaling pathway" indicates that some or all of the components of the signaling pathway are naturally-occurring components of the cell. An example of such a pathway is the endogenous pheromone system pathway of yeast.

The term "functionally couples to" (as in a receptor that is "functionally integrated into a signaling pathway in a cell" or "functionally integrated into an endogenous yeast signaling pathway") is intended to refer to the ability of the receptor to be expressed at the surface of the cell and the ability of the expressed receptor to bind to modulators (e.g., a ligand of the receptor) and transduce signals into the cell via components of a signaling pathway of the cell. For example, a G protein coupled receptor (GPCR) which is functionally integrated into an endogenous pheromone response or signaling pathway of a yeast cell is expressed on the surface of the yeast cell, couples to a G protein of the pheromone response pathway within the yeast cell and transduces a signal in that yeast cell upon binding of a modulator to the receptor. For example, a G protein subunit, e.g., a chimeric, mutant or heterologous subunit, that is functionally integrated into a yeast cell may be capable of coupling both to the GPCR and to the other G protein subunits, which can also be endogenous to the yeast cell, can be chimeric, or can be heterologous. Alternatively, the G protein subunit can be constitutively active such that it need not be coupled to a heterologous GPCR. A transduced signal may be detected by measuring any one of a number of responses to mating factors which occur in a yeast cell, e.g., growth airest or transcription of an indicator gene responsive to signals produced by modulation of a pheromone system pathway or any biochemical changes.

The term "indicator gene" generically refers to an expressible (e.g., able to transcribed and (optionally) translated) DNA sequence which is expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

An endogenous gene that is to be used as an indicator gene may comprise the natural regulatory elements of the gene (e.g., the native promoter/enhancer elements that naturally regulate expression of the gene) or the endogenous gene can be "operatively linked to" (i.e., functionally coupled to) a "heterologous promoter" (or other heterologous regulatory elements). A "heterologous promoter" refers to a promoter that does not naturally regulate the gene to which the heterologous promoter is operatively linked. For example, an endogenous yeast gene that is not normally pheromone-responsive can be operatively linked to a heterologous promoter that is responsive to signals produced by the yeast pheromone system to thereby confer pheromone responsiveness on the endogenous yeast gene. Methods of using endogenous yeast genes as indicator genes are described further in PCT Publication WO 98/13513 the contents of which are hereby expressly incorporated herein by this reference.

The term "detecting an alteration in a signal produced by an endogenous signaling pathway" (e.g., an endogenous yeast signaling pathway) is intended to encompass the detection of alterations in endogenous second messengers produced upon activation of components of the endogenous signaling pathway, alterations in endogenous gene transcription induced upon activation of components of the endogenous signaling pathway, and/or alterations in the activity of an endogenous protein(s) upon activation of components of the endogenous signaling pathway. In certain embodiments, the term "detecting an alteration in a signal produced by an endogenous signaling pathway" can also encompass assaying general, global changes to the cell such as changes in cell growth or cell morphology.

As used herein, a "reporter gene construct" refers to a nucleic acid that includes a "reporter gene" operatively linked to a transcriptional regulatory sequences. Transcription of the reporter gene is controlled by these sequences. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences which are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nuclcotides that alter translation of the resulting mRNA, thereby altering the amount of reporter gene product. The reporter gene constructs of the present invention provide a detectable readout in response to signals transduced in response to modulation of a heterologously expressed receptor.

The term "modulation", as in "modulation of a (heterologous) receptor" and "modulation of a signal transduction activity of a receptor protein" is intended to encompass, in its various grammatical forms, induction and/or potentiation, as well as inhibition and/or downregulation of receptor activity and/or one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand or otherwise modulating the activity of the receptor, for example, by influencing the activity of components which regulate the receptor, or which function in the signal transduction pathway initiated by the receptor. Receptor effectors can modulate signal transduction when used alone, i.e. can be surrogate ligands, or can alter signal transduction in the presence of the natural ligand or other known activators, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The term "surrogate ligand" refers to an agonist which induces signal transduction from a receptor.

The term "autocrine cell", as used herein, refers to a cell which produces a substance which can stimulate a receptor located on or within the same cell as that which produces the substance. For example, wild-type yeast MATα and MATa cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

As used herein, the term "not produced in functional form" with regard to endogenous yeast proteins is intended to encompass proteins which are not produced in functional form for any number of reasons, for example, because of a mutation to the gene which encodes the protein or a deletion e.g., a disruption, of the gene which encodes the protein. The term "not produced in functional form" is also intended to include conditional mutations (e.g. temperature sensitive mutation), wherein the protein is not produced in functional form under certain conditions. The term also includes proteins (e.g., in a mutant yeast cell) that are not folded correctly (i.e., the tertiary structure doesn't resemble that of the protein when normally expressed in functional form).

II. General Overview of Assay

As set out above, the present invention relates to yeast cell compositions and methods for identifying effectors of a receptor protein or receptor protein complex. The instant assays are characterized by the use of a mixture of recombinant yeast cells to sample test compounds for receptor agonists or antagonists. As described in greater detail below, the reagent cells express a heterologous GPCR protein functionally integrated into the cell and capable of transducing a detectable signal in the yeast cell. Exemplary GPCRs are discussed below. Compounds which either agonize or antagonize the receptor function can be selected and then identified based on biochemical signals produced by the receptor, or any more distal result of receptor-mediated stimulation, for example increases in endogenous mRNA expression, etc., or, in some embodiments, by the use of reporter genes responsive to such signals. In certain embodiments, the library of compounds to be tested is a library of peptides which is expressed by the yeast cells and causes stimulation in an autocrine fashion.

The ability of compounds to modulate the signal transduction activity of the target receptor can be scored for by detecting up or down-regulation of the detection signal. For example, GTPase activity, phospholipid hydrolysis, or protein phosphorylation stimulated by the receptor can be measured directly. Alternatively, the use of a reporter gene can provide a readout. In any event, a statistically significant change in the detection signal can be used to facilitate isolation of compounds of interest.

As discussed in more detail below, the instant yeast cells comprise a mutation in the STP22 gene such that the STP22 gene product is inactivated. The use of yeast cells with this background results in enhanced signaling via heterologous receptors. Although the precise role of the product of the STP22 gene has not been established, the protein is believed to be involved in control of protein transport from the prevacuolar compartment to the vacuole. Although not intending to be limited by mechanism, it is thought that the stp22 mutant yeast host cells that express a heterologous G protein receptor exhibit the improved property of enhanced signaling upon modulation of the receptor, as compared to wild type yeast cells, because the stp22 mutation inhibits (or prevents) the mislocalization of the receptor to the vacuole, thereby promoting increased expression at the receptor to the yeast plasma membrane or at the cell surface.

In certain embodiments, the yeast cells for use in the instant assays express heterologous GPCR and an endogenous (G protein subunit which couples to that receptor. Preferably, the yeast cells of the present invention have been modified such that coupling of the GPCR to the yeast pheromone signaling pathway is enhanced. For example, in preferred embodiments the yeast cells express a heterologous GPCR and mutated endogenous G protein subunit which facilitates functional integration of that receptor into the yeast cell. In another preferred embodiment the yeast cells express a heterologous GPCR and a heterologous G protein subunit. In particularly preferred embodiments, the heterologous GPCR and the heterologous G protein subunit are of the same origin, e.g., mammalian. In yet another preferred embodiment, the yeast cells express a mutated heterologous G protein subunit.

In still another preferred embodiment, the yeast cells express a chimeric G protein subunit. In particularly preferred embodiments the heterologous GPCR and the heterologous segment of the chimeric G protein subunit are derived from the same source. In more preferred embodiments, the second amino acid sequence in the G protein subunit chimera is derived from a mammalian G protein subunit. In particularly preferred embodiments, the second amino acid sequence is derived from a human G protein subunit sequence.

It will further be understood that the above embodiments are not mutually exclusive. For example, in certain preferred embodiments, a yeast cell may have an stp22 mutation and may express a first mutated or chimeric G protein subunit and a second, different mutated or chimeric G protein subunit to enhance coupling to the heterologous receptor.

In certain embodiments the yeast cells also express an indicator gene that produces a detectable signal upon functional coupling of the heterologous G protein coupled receptor to the G protein. In certain embodiments the indicator gene is a reporter gene construct which including a reporter gene in operative linkage with one or more transcriptional regulatory elements responsive to the signal transduction activity of the target receptor, with the level of expression of the reporter gene providing the receptor-dependent detection signal. The amount of transcription from the reporter cene may be measured using any method known to those of skill in the art. For example, specific mRNA expression may be detected using Northern blots or specific protein product may be identified by a characteristic stain or an intrinsic activity. In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of activation of the indicator gene, e.g., expression of a reporter gene, is then compared to the amount of expression in either the same cell in the absence of the test compound or it may be compared with the amount of transcription in a substantially identical cell that lacks the specific receptors or that expresses a different receptor (e.g., a different GPCR that couples to the same Gα subunit as the test GPCR). A control cell may be derived from the same cells from which the recombinant cell was prepared but which had not been modified by introduction of heterologous DNA, e.g., the encoding a test polypeptide. Alternatively, it may be a cell in which the specific receptors are removed. Any difference, e.g., a statistically significant difference, in the amount of transcription indicates that the test compound has in some manner altered the activity of the specific receptor.

In other preferred embodiments, the reporter gene provides a selection method such that cells in which the compound is an effector for the receptor have a growth advantage. For example the reporter could enhance cell viability, relieve a cell nutritional requirement, and/or provide resistance to a drug.

By using any one of these readouts, compounds which modulate signaling via the heterologous receptor can be selected. If the compound does not appear to modulate signaling via the receptor protein, the assay may be repeated and modified by the introduction of a step in which the recombinant cell is first contacted with a known activator of the target receptor to induce signal transduction from the receptor, and the compound is assayed for its ability to inhibit the activity of the receptor, e.g., to identify receptor antagonists. In yet other embodiments, compounds can be screened for members which potentiate the response to a known activator of the receptor.

III. stp22 Mutant Strains

The invention generally provides compositions and methods that provide enhanced signaling, via the pheromone response pathway, through heterologous G protein coupled receptors expressed in yeast cells that have a mutation that renders an endogenous yeast Stp22 protein nonfunctional. The invention provides a recombinant yeast cell having an endogenous yeast pheromone system pathway which yeast cell comprises:

(i) a heterologous G protein coupled receptor which functionally couples to the endogenous yeast pheromone system pathway; and (ii) a mutation which renders an endogenous yeast Stp22 protein nonfunctional.

Preferably, the heterologous G protein coupled receptor is a mammalian G protein coupled receptor. Even more preferably, the heterologous G protein coupled receptor is a human G protein coupled receptor.

Although not intending to be limited by mechanism, it is thought that the stp22 mutant yeast host cells that express a heterologous G protein receptor exhibit the improved property of enhanced signaling upon modulation of the receptor, as compared to wild type yeast cells, because the stp22 mutation inhibits (or prevents) the mislocalization of the receptor to the vacuole, thereby promoting increased expression or delivery of the receptor to the yeast cell surface membrane. It has been postulated that the yeast vacuolar membrane proteins are delivered from the Golgi apparatus to their final destination by a default pathway (Nothwehr, S. F., and Stevens, T. H. (1994) *J. Biol. Chem.* 269, 10185–10188 and references cited therein). According to this hypothesis, the plasma membrane proteins possess specific structural determinants of unknown nature that serve as sorting signals promoting protein transport to the cell surface. Some proteins may be transported to the vacuole because they lack proper sorting information. Consistent with this idea, it has been demonstrated that some mutant species of yeast plasma membrane proteins, such as Ste2p (Jenness, D. D., Li, Y., Tipper, C., and Spatrick, P. (1997) *Mol. Cell. Biol.* 17, 6236–6245) and Pmalp (Luo, Wj, and Chang, A. (1997) *J. Cell. Biol.* 138, 731–746.) are mislocalized to the vacuole. Furthermore, the human dopamine receptor expressed in yeast was shown to be predominantly associated with the vacuolar compartment (Sander, P., Grunewald, S., Bach, M., Haase, W., Reilander, H., and Michel, H. (1994) *Eur. J. Biochem.* 226, 697–705).

A family of approximately fifty VPS genes have been implicated in the control of vacuolar protein transport in *S. cerevisiae* (for review see Conibear, E., and Stevens, T. H. (1995) Cell 83, 513–516; Stack, J. H., Horazodvsky, B., and Emr, S. D. (1995) Annu. Rev. Cell Dev. Biol. 11, 1–133). Inactivation of any of those genes results in rerouting of the vacuolar proteins to the cell surface. Most of the vps mutations, however, cause severe growth defects at 30° C. and lethality at higher temperatures. Moreover, some mutations were found to downregulate the pheromone response pathway (Dulic, V. and Riezman, H. (1991) *J. Cell. Sci.* 97:517–525). Both of these phenotypes are incompatible with high throughput screening assays.

In contrast, these problems do not occur in stp22 mutant strains. The stp22 mutation was isolated as a suppressor of a mating defect of the ste2-3ts mutation (Cartwright, C. P., and Tipper, D. J. (1991) *Mol. Cell. Biol.* 11, 9620–2628.). It has since been demonstrated that this mutation reroutes the mutant Ste2 receptor and some other mutant plasma membrane proteins as well as a vacuolar protein carboxypeptidase Y from the vacuole to the cell surface (Li, Y., Kane, T., Tipper, C., (1997) Abstracts of Yeast Cell Biology Meeting, Cold Spring Harbor laboratory, Cold Spring Harbor, N.Y.). The precise biological role of the product of STP22 gene has not yet been established. however, the protein is believed to be involved in control of protein transport from the prevacuolar compartment to the vacuole. Intriguingly, it possesses a region showing high sequence similarity to the catalytically inactive homologs of ubiquitin-conjugating enzymes (E2) that may represent a family of the dominant negative regulators of protein tibiquitination (Koonin, F. V., and Abagyan, R. A. (1997) *Nature Genetics* 16, 330–331).

At least two characteristic features of the stp22 mutant strains make them the appropriate candidates for the development of GPCR functional growth assays. First, a knockout of STP22 gene causes only a mild temperature-sensitive growth defect. Second, since stp22 mutation was shown to restore mating competence of the ste2-3ts strains, it does not appear to negatively affect the pheromone response. As demonstrated in the Examples, a variety of heterologous G protein coupled receptors expressed in stp22 yeast cells display enhanced ligand-induced growth activation as compared to isogenic wild type strain expressing the receptor.

To express the heterologous GPCR in the cell membrane of the yeast host cell, a number of alternative approaches can be used with regard to the presence or absence of a leader sequence. For example, in one embodiment, the heterologous GPCR contains a native leader sequence and this native leader sequence of the GPCR can be used (i.e., the receptor's own, natural leader sequence can be used to express the heterologous GPCR in the yeast cells). In another embodiment, the heterologous GPCR may not itself contain a native leader sequence and thus the GPCR can be expressed in its native form without a leader sequence (see e.g., Example 3 regarding expression of the native human MCR4 receptor). In yet another embodiment, an unrelated leader sequence (i.e., a leader sequence that is heterologous to the GPCR, such as a yeast leader sequence with a mammalian GPCR) can be used to express the heterologous G protein coupled receptor. This unrelated leader sequence can be, for example, added to a heterologous GPCR that does not itself contain a leader sequence, or can replace the native leader sequence of a heterologous GPCR that itself contains a leader sequence, or can be added in tandem to a heterologous GPCR that itself contains a leader sequence (such that the resultant construct contains both the unrelated leader and the native leader). It should be noted, however, that a certain heterologous leader sequence (the yeast α-factor leader) is not preferred for use with the stp22 background (discussed further below).

Examples of heterologous leader sequences that can be used include the leader sequence of the yeast Ste2 receptor and the invertase leader sequence. The leader sequence of yeast α-factor is often used to express heterologous receptors in yeast cells and, for at least certain receptors, may be amenable to use with stp22 yeast cells. However, for at least certain receptors, use of an α-factor leader sequence in combination with the stp22 mutation leads to decreased ligand-induced growth activation (see the Examples, in particular Example 5) and therefore, in certain preferred embodiments, the heterologous G protein coupled receptor is expressed in the yeast cell using a leader sequence other than an α-factor leader sequence.

Preferred heterologous GPCRs for use in the invention include the following receptors: human nociceptin receptors, human melanocortin receptors (e.g., hMCR4 or hMCR5), human somatostatin receptors (e.g., hSSTR2 or hSSTR3) and human corticotropin releasing receptors (e.g., hCRFR1 or hCRFR2α).

In addition to the stp22 mutation, yeast host cells of the invention can comprise other additional modifications (e.g., expression of a heterologous or chimeric G protein subunit), which modifications are described in other sections of the application.

The stp22 yeast cells expressing a heterologous GPCR can be used in screening assays to identify modulators of the receptor. Accordingly, in one embodiment, the invention provides a method of identifying compounds which modulate a G protein coupled receptor, comprising the steps of:
 a) providing a yeast cell which comprises:
  (i) a heterologous G protein coupled receptor which functionally couples to the yeast pheromone system pathway; and
  (ii) a mutation which renders an endogenous yeast Stp22 protein nonfunctional;
 b) contacting the yeast cell with a compound
 c) identifying compounds which induce a change in a detectable signal in the yeast cell, wherein said detectable signal indicates that the compound is a modulator of the heterologous G protein coupled receptor.

Ways of monitoring changes in a detectable signal in the yeast host cells (e.g., using a reporter gene) are described in detail in other sections of the application. Moreover, types of compounds (e.g., various libraries of compounds) that can be screened using the assay are described in detail in other sections of the application.

Standard techniques for manipulating yeast genes (e.g., by homologous recombination) can be used to create stp22 mutant yeast cells for use in the invention. The sequence of the stp22 gene is known in the art and can be found, e.g., on GenBank (Li et al. 1997; accession No. AF004731). Exemplary constructs and techniques for making the yeast host cells of the invention are described in further detail in the Examples.

IV. Host Cells

The host cells of the present invention may be of any species of yeast which are cultivable and in which an exogenous receptor can be made to engage the appropriate signal transduction machinery of the host cell. Exemplary species include *Kluyverei lactis, Schizosaccharomyces pombe,* and *Ustilago maydis,* with *Saccharomyces cerevisiae* being preferred. Other yeast which can be used in practicing the present invention are *Neurospora crassa, Aspergillus niger, Aspergillus nidulans, Pichia pastoris, Candida tropicalis,* and *Hansenular polymorpha.* The term "yeast", as used herein, includes not only yeast in a strictly taxonomic sense, i.e., unicellular organisms, but also yeast-like multicellular fungi or filamentous fungi.

V. Expression Systems

In general it will be desirable that an expression vector be capable of replication in the host cell. Heterologous DNA may be integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, N.Y., 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Suitable promoters for function in yeast include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphogylycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrooenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In certain embodiments, it will be desirable to control the copy number of the heterologous gene which is expressed. For example, in certain embodiments, expression of a gene which results in activation of the pheromone response pathway will be from a low copy number in order to better detect ligand induced signaling. Exemplary low copy number plastids suitable for use in yeast cells are known in the art and include, e.g., ARS vectors or centromeric sequences (CEN) (See e.g., Romanos et al. 1992. *Yeast* 8:423). In other embodiments, however, the use of high copy number plasmids will be desirable. Exemplary high copy number plasmids are also known in the art and include *E. coli*-yeast shuttle vectors based on 2μ. In yet other embodiments it may be desirable to express heterologous DNA in a yeast cell using integrating vectors, such as YIp vectors. The use of high DNA concentrations of integrating vectors can result in tandem multicopy inserts due to repeated recombination events. Alternatively, heterologous DNA can be integrated into reiterated chromosomal DNA to generate stable multicopy integrants (Kingsman et al. 1985. *Biotechnol. Genet. Eng. Revs.* 3:377; Lopes et al. 1989. *Gene* 79:199)

VI. Receptors

Numerous different receptor types can be expressed in yeast cells for use in the instant invention.

The "heterologous receptors" of the present invention may be any G protein-coupled receptor which is exogenous to the cell which is to be genetically engineered for the purpose of the present invention. This receptor may be, for example, a plant or animal cell receptor. Screening for binding to plant cell receptors may be useful in the development of, e.g., herbicides. In the case of an animal receptor, it may be of invertebrate or vertebrate origin. An invertebrate receptor would, for example, facilitate development of insecticides. The expression of a receptor from a different species of yeast is also included within the term "heterologous" and could be used in the development of fungicides. The receptor may also be a vertebrate, more preferably a mammalian, still more preferably a human, receptor. The exogenous receptor is also preferably a seven transmembrane segment receptor.

Known ligands for GPCRs include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, sub stance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include: α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopanline receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptidc receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, ncuropeptide Y receptor, amyloid protein precursor receptor, insulin-like growth factor II receptor, bradykinin receptor, gonadotropin-relcasing hormone receptor, cholecystokinin receptor, melanocyte stimulating hormone receptor, antidiuretic hormone receptor, glucagon receptor, and adrenocorticotropic hormone II receptor.

Other suitable receptors are known in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Thus, for expression in yeast, the gene could be operably linked to a promoter functional in the cell to be engineered and to a signal sequence that also functions in the cell. For example, suitable promoters include Ste2, Ste3 and gal10. Optionally, the codons of the gene would be optimized for expression in yeast. See Hockema et al.,(1987) *Mol. Cell. Biol.*, 7:2914–24; Sharp, et al., (1986) 14:5125–43.

In some instances a foreign receptor which is expressed in yeast will functionally integrate into the yeast membrane, and there interact with the endogenous yeast G protein. In other instances, either the receptor may be modified or a compatible G protein or a chimeric (i.e., part yeast/part mammalian) G protein subunit which can properly interact with the exogenous receptor G protein may be provided. The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergtent. The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites. Such information can be useful in creating mutations in GPCRs to enhance functionality.

If a naturally occurring exogenous GPCR cannot be made functional in yeast, it may be mutated for this purpose. For example, a comparison can be made of the amino acid sequences of the exogenous receptor and of the yeast receptors, and regions of high and low homology identified. Trial mutations can be made to distinguish regions involved in ligand or G protein binding, from those necessary for functional integration in the membrane. The exogenous receptor can then be mutated in the latter region to more closely resemble the yeast receptor, until functional integration was achieved. If this were insufficient to achieve functionality, mutations could next be made in the regions involved in G protein binding. Alternatively, the naturally occurring exogenous GPCR can be mutated to more closely resemble another mammalian receptor that is known to functionally integrate in yeast cells or random mutagenesis can be performed followed by selection of mutants that can functionally integrate in the yeast cells. Another possible approach for achieving functional integration of the receptor is to make a chimeric receptor (mammalian/yeast)(see e.g., U.S. Pat. No. 5,576,210 issued to Sledziewski et al).

Preferably, the yeast genome is modified so that it is unable to produce the yeast receptors which are homologous to the exogenous receptors in functional form in order to facilitate assay interpretation. For example, the endogenous G protein or G protein subunit is mutated generating, for example, a temperature sensitive mutant.

GPCR Expression

In other embodiments, a secretory signal of a yeast protein can be used to direct transport of the receptors, for example G protein coupled receptors, to the plasma membrane as described in the appended examples. Previous work has demonstrated the secretory expression of foreign proteins in yeast cells using the signal sequence of a yeast secreted protein such as invertase or acid phosphatase, encoded by the SUC2 and PHO5 genes, respectively (Schraber, M. D. et al. (1986) *Methods Enzymol.* 119:416; Moir, D. T. et al. (1991) *Methods Enzymol.* 194:491–507). The vast majority of the secreted proteins possess a hydrophobic N-terminal signal sequence which targets them to the endoplasmic reticulum. A leader sequence of the α-factor precursor encoded by the MFα1 gene was shown to promote the most efficient secretion of various heterologous proteins. In addition to a signal sequence, the α-factor leader includes a hydrophilic pro-region which is believed to facilitate protein transport at the later stages of the secretory pathway.

Both secreted and membrane proteins including G protein coupled receptors are delivered to the cell surface through the same secretory pathway. Some receptors, for example, metabotropic glutamate receptors and vasoactive intestinal peptide receptors, also possess the N-terminal signal sequence, whereas some do not. In the latter case, a first transmembrane domain is believed to interact with the ER translocation machinery. The use of yeast secretory signals, in particular, the α-factor leader, may be desirable to provide the more efficient integration of the receptors into the membrane of the endoplasmic reticulum and transport to the plasma membrane. In fact, the cell surface expression of the rat M5 receptor directed by the α-factor leader has been documented (Huang et al. (1992) *Biochem. Biophys. Res. Commun.* 181:1180).

VII. G Protein Subunits and Complexes

In certain instances it will be desirable to modify naturally occurring forms of yeast or mammalian G-protein subunits. For instance, where a heterologous GPCR does not adequately couple to the endogenous yeast G protein subunit, such a subunit, e.g., GPA1 may be modified to improve coupling. Such modifications can be made by mutation, e.g., directed mutation or random mutation, using methods known in the art and described in more detail below.

Alternatively, a heterologous subunit can be expressed. The specificity of coupling of a receptor to a heterotrimeric G-protein is largely determined by the α subunit of the G-protein. Thus, in preferred embodiments, a heterologous Gα subunit is expressed in the yeast cell. The predominant role of the yeast Gα, GPA1, is to bind to and sequester the effector-signaling βγ component of the heterotrimer. Thus, in order to achieve functional integration into a yeast pheromone signaling pathway, a heterologous Gα subunit must bind to yeast βγ in the quiescent state, and release it upon receptor activation.

If functional integration is not achieved, or is not optimal, the heterologous subunit can be mutated. For example, in general, mammalian Gα subunits couple poorly to the βγ subunits of yeast cells. In yeast which lack their own endogenous Gα subunit, this failure to couple results in the constitutive activation of the pheromone pathway due to the effector activity of the unbound yeast βγ. Accordingly, if a naturally occurring heterologous G protein subunit does not enhance coupling, modifications can be made. Such modifications may take the form of mutations which are designed to increase the resemblance of the G protein subunit to the yeast G protein subunit while decreasing its resemblance to the heterologous receptor-associated G protein subunit.

For example, a residue may be changed so as to become identical to the corresponding yeast G protein residue, or to belong to the same exchange group of that residue. After modification, the modified G protein subunit might or might not be "substantially homologous" to the heterologous and/or the yeast G protein subunit.

In the case of Gα, modifications are preferably concentrated in regions of the Gα which are likely to be involved in Gβγ binding.

In other embodiments, modifications will take the form of replacing one or more amino acids of the receptor-associated G protein subunit with the corresponding yeast G protein subunit amino acids, thereby forming a chimeric G protein subunit. In preferred embodiments, three or more consecutive amino acids are replaced. In other embodiments, point mutations may be sufficient.

Chimeric G protein subunits of the invention enhance coupling of the heterologous receptor to the endogenous yeast signaling pathway. For example, a chimeric Gα subunit will interact with the heterologous receptor and the yeast Gβγ complex, thereby permitting signal transduction.

A yeast cell of the present invention can express one or more of the indicated G protein structures. For example, a yeast cell can express a chimeric Gα subunit, and an endogenous yeast Gβγ, a mammalian Gβγ, a mutated mammalian Gβγ, or a chimeric Gβγ.

In preferred embodiments, both the receptor and the heterologous subunit are derived from the same source, e.g., are mammalian. In particularly preferred embodiment, both are human in origin.

In another preferred embodiment, a yeast cell that expresses a heterologous or chimeric G protein subunit has been modified such that the endogenous, homologous G protein subunit gene is disrupted.

In certain embodiments, yeast strains lacking pheromone receptors and having no heterologous receptor capable of coupling to the pheromone response pathway may be used to assess the affinity of an endogenous yeast G protein subunit, a mammalian G protein subunit, a mutated G protein subunit, or chimeric G protein subunit for other yeast subunits. For example, the affinity of gpa1p, chimeric gpa-Gα s, or other Gα subunit for yeast βγ or other chimeric βγ subunit can be assessed. Such strains depend on free βγ for signaling through the pheromone response pathway leading to growth arrest. Mutant Gα subunits may be tested in such a system, those which bind βγ more effectively will sequester βγ and reduce or block signaling. Preferably, such chimeras and gpa1 subunits can be assessed in a gpa1⁻ background to avoid competition w,ith gpa1 for βγ. For example. Cα s chimeric mutants (see below) carrying D229S. E10K, N254D, or S286P were found to sequester βγ more effectively than the chimera with wild type sequences. Also, double mutants were even more effective than either single mutant. Similarly, overexpression of Gαs by driving transcription from the highly efficient PGK promoter resulted in dampening of the receptor coupling which may be offset by introduction of the double mutant Gαs (D229S, E10K).

Guidance for making mutations in G protein subunits and in the construction of chimeric G protein subunits is provided below.

Site-Directed Mutagenesis Versus Random Mutagenesis

There are numerous art recognized ways to solve the structure-function problems of the sort presented by attempts to define the determinants involved in mediating the association of the subunits that comprise the G protein heterotrimer. For example, in one approach, discussed above with respect to hybrid constructs, specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes.

With random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. α-helices, β-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele.

Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing, the molecule in a step-wise faslion, i.e. mutating one linear cassette of residues at a time and then assaying for function.

The present invention provides for applying random mutagenesis in order to further delineate the determinants involved in Gα-Gβγ or subunit-receptor association. Random mutagenesis may be accomplished by many means, including:

1. PCR mutageniesis, in which the error prone Taq polymerase is exploited to generate mutant alleles of G protein subunits, which are assayed directly in yeast for an ability to couple.

2. Chemical mutagenesis, in which expression cassettes encoding G protein subunits are exposed to mutagens and the protein products of the mutant sequences are assayed directly in yeast for an ability to couple.

3. Doped synthesis of oligonucleotides encoding portions of the G protein subunit gene.

4. In vivo mutagenesis, in which random mutations are introduced into the coding region of G protein subunits by passage through a mutator strain of *E. coli*, XL1-Red (mutD5 mutS mutT) (Stratagene, Menasa, Wis.).

In certain embodiments, for example, the random mutagenesis may be focused on regions suspected to be involved in Gα-Gβγ association. Random mutagenesis approaches are feasible for two reasons. First, in yeast one has the ability to construct stringent screens and facile selections (growth vs. death, transcription vs. lack of transcription) that are not readily available in mammalian systems. Second, when using, yeast it is possible to screen efficiently through thousands of transformants rapidly. For example, this relatively small region of Gα subunits represents a reasonable target for cassette mutagenesis. Another region that may be amenable to cassette mutagenesis is that defining the surface of the switch region of Gα subunits that is solvent-exposed in the crystal structures of Gαi and transducin. From the data described below, this surface may contain residues that are in direct contact with yeast Gβγ subunits, and may therefore be a reasonable target for mutagenesis.

A. Modification of Gα

Some aspects of Gα structure are relevant to the design of modified Gα subunits. Alignments of Gα and GPA1 can be made to determine sequence similarity. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc. Natl. Acad Sci USA* 84:5115–5119). An alignment of GPA1 and four other Gα proteins is provided by Stone and Reed (1990. Mol. Cell Biol. 10:4439).

The gene encoding a G protein homolog of *S. cerevisiae* was cloned independently by Dietzel and Kurjan (supra) (who referred to the gene as SCG1) and by Nakafuku, et al. (1987 *Proc Natl Acad Sci* 84:2140–2144) (who called the gene GPA1). Sequence analysis revealed a high degree of homology between the protein encoded by this gene and mammalian Gα. GPA1 encodes a protein of 472 amino acids, as compared with approximately 340–350 amino acids for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to Gαs (33% identity, or 51% with conservative substitutions) (Nakafuku, et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein synthesis elongation factor EF-Tu. This highly conserved guanine nucleotide-binding domain consists of a six-stranded β sheet surrounded by a set of five α-helices. It is within these β sheets and α helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP- and GTPγS-liganded forms of bovine rod transducin (Noel, et al. (1993) *Nature* 366:654–663); (Lambright, et al. (1994) *Nature* 369:621–628), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick, et al. (1992) *Science* 256:1031–1033); (Artemyev, et al. (1992) *J. Biol. Chem.* 267:25067–25072), while a "GAP-like" activity has been ascribed to the largely α-helical insert 1 domain of GαS (Markby, et al. (1993) *Science* 262:1805–1901).

While the amino- and carboxy-termini of Gα subunits do not share striking homology either at the primary, secondary, or tertiary levels, there are several generalizations that can be made about them. First, the amino termini of Gα subunits have been implicated in the association of Gα with Cβγ complexes and in membrane association via N-terminal myristoylation. In addition, the carboxy-termini have been implicated in the association of Gαβγ heterotrimeric complexes with G protein-coupled receptors (Sullivan, et al. (1987) *Nature* 330:758–760); West, et al. (1985) *J. Biol. Chem.* 260:14428–14430); (Conklin, et al. (1993) *Nature* 363:274–276); (Kallal and Kurjan. 1997. *Mol. Cell. Biol.* 17:2897). Data in support of these generalizations about the function of the N-terminus derive from several sources, including both biochemical and ogenetic studies.

In the GPA41Gα hybrids, the amino terminal 41 residues are derived from GPA1. All residues following position 41 are contributed by the human Gα subunits, including the consensus nucleotide binding motif. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119).

There is little if any sequence homology shared among the amino termini of Gα subunits. The amino terminal domains of Gα subunits that precede the first β-sheet vary in length from 41 amino acids (GPA1) to 31 amino acids (Gαt). Most Gα subunits share the consensus sequence for the addition of myristic acid at their amino termini, although not all Gα subunits that contain this motif have myristic acid covalently associated with the glycine at position 2 (Speigel, et al. (1991) *TIBS* 16:338–3441). The role of this post-translational modification has been inferred from studies in which the activity of mutant Gα subunits from which the consensus sequence for myristoylation has been added or deleted has been assayed (Mumby et al. (1990) *Proc. Natl. Acad. Sci. USA* 87: 728–732; (Linder, et al. (1991) *J. Biol Chem.* 266:4654–4659); Gallego, et al. (1992) *Proc. Natl. Acad. Sci. USA* 89:9695–9699). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene products, at present is unknown.

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/or to activate effector molecules. In all cases, Gα subunits with truncated amino termini were deficient in all three functions (Graf, et al. (1992) *J. Biol. Chem.* 267:24307–24314); (Journot, et al. (1990) *J. Biol. Chem.* 265:9009–9015); and (Neer, et al. (1988) *J. Biol. Chem* 263:8996–9000). Slepak, et al. (1993, *J. Biol. Chem.* 268:1414–1423) reported a mutational analysis of the N-terminal 56 a.a. of mammalian Gαo expressed in *Escherichia coli*. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin. Other work has revealed specific amino acid residues of CPA1 that are important in GPA1 function. For example, a E307K mutation appears to create an α subunit with a broadened specificity for Gβ subunits (Whiteway et al. 1994. Mol. Cell. Biol. 14:3223). Interestingly, the residue in the mammalian α subunit which is equivalent to the E307 position is diagnostic for a particular class of mammalian α subunits. For example, the $G_s\alpha$ subunits contain a lysine at this position, the $G_o$ and $G_i\alpha$ subunits contain a histidine, the transducin α subunits have a glutimine, the $G_q\alpha$ subunits have a proline, and the $G_{13}$ a subunits have an aspartic acid at this site (Whiteway et al. supra).

Genetic studies examined the role of amino-terminal determinants of Gα in heterotrimer subunit association have been carried out in both yeast systems using GPA1-mammalian Gα hybrids (Kang, et al. (1990) *Mol. Cell. Biol.* 10:2582–2590) and in mammalian systems using Gαi/Gαs hybrids (Russell and Johnson (1993) *Mol. Pharmacol.* 44:255–263). In the former studies, gene fusions, composed of yeast GPA1 and mammalian Gα sequences were constructed by Kang, et al. (supra) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gαo proteins are competent to associate with yeast Gα and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit α-factor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems (Russell and Johnson (supra). In these studies, a large number of chimeric Gα subunits were assayed for an ability to activate adenylyl cyclase and therefore, indirectly, for an ability to interact with Gβγ (i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the β sheet identified in the crystal structure of Gαt (see Noel. et al. supra and Lambright, et al. supra) are involved in determining the state of activity of the heterotrimer by (1) driving association/dissociation between Gα and Cβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

B. Construction of Chimeric Gα Sutunits.

In preferred embodiments chimeric Gα subunits retain as much of the sequence of the native mammalian proteins as possible and, in particularly preferred embodiments, the level of expression for the heterologous components should approach, as closely as possible, the level of their endogenous counterparts. The results described by King, et al. (1990, Science 250:121–123) for expression of the human β2-adrenergic receptor and Gαs in yeast, taken together with negative results obtained by Kang, et al. (supra) with full-length mammalian Gα subunits other than Gαs, led to the following preferred embodiments for the development of yeast strains in which mammalian G protein-coupled receptors could be linked to the pheromone response pathway.

In one embodiment, mammalian Gα subunits are expressed using the native sequence of each subunit or, alternatively, as minimal gene fusions with sequences from the amino-terminus of GPA1 replacing the homologous residues from the mammalian Gα subunits. In another embodiment, mammalian Gα subunits are expressed from the GPA1 promoter either on low copy plasmids or after integration into the yeast genome as a single copy gene. In certain embodiments, endogenous Gβγ subunits are provided by the yeast STE4 and STE18 loci, while in other embodiments chimeric or heterologous Gβ and/or Gγ subunits are also provided.

C. Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes GPA$_{BAMH1}$, GPA$_{41}$, GPA$_{ID}$, and GPA$_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, from the amino terminus of the yeast Gα, is fused to a sequence from a mammalian (or other exogenous) Gα. While about 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

i. GPA$_{BAMH1}$ Hybrids.

Kang et al. supra. described hybrid Gα subunits encoding the amino terminal 310 residues of GPA1 fused to the carboxyl terminal 160, 143 and 142 residues, respectively, of GαS, Gαi2, and Gαo. In all cases examined by Kang et al., the hybrid proteins were able to complement the growth arrest phenotype of gpa1 strains. Hybrids between GPA1 and Gαi3, Gαq and Gα16 can be constructed, as described below, and functionally complement the growth arrest phenotype of gpa1 strains.

GPA41 hybrids: The rationale for constructing a minimal hybrid encoding only 41 amino acids of GPA1 relies upon the biochemical evidence for the role of the amino-terminus of Gα subunits discussed above, together with the following observation. Gβ and Gγ subunits are known to interact via α-helical domains at their respective amino-termini (Pronin, et al. (1992) *Proc. Natl. Acad. Sci. USA* 89:6220–6224); Garritsen, et al. 1993). The suggestion that the amino termini of Gα subunits may form an helical coil and that this helical coil may be involved in association of Gα with Gβγ (Masters et al (1986) *Protein Engineeiring* 1:47–54); Lupas et al.(1992) *FEBS Lett.* 314:105–108) leads to the hypothesis that the three subunits of the G-protein heterotrimer interact with one another reversibly through the winding and unwinding of their amino-terminal helical regions. (For further description of the crystal structure of G proteins, and subunits thereof, see Lambright et al. (1996) *Nature* 379:311–319 and Sondek et al. (1996) *Nature* 379:369–374.) A mechanism of this type has been suggested, as well, from an analysis of leucine zipper mutants of the GCN4 transcription factor (Harbury, et al. (1993) *Science* 262:1401–1407). The rationale for constructing hybrids like those described by Kang, et al. supra., that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signaling pathway in yeast.

GPA$_{41}$ hybrids that have been constructed and tested include Gαs, Gαi2, Gαi3, Gαq, Gαo$_a$, Gαo$_b$ and Gα16. Hybrids of Gαs, Gαi2, Gαi3, and Gα16 functionally complement the growth arrest phenotype of gpa1 strains, while GPA$_{41}$ hybrids of Gαo$_a$ and Gαo$_b$ do not. In addition to being tested in a growth arrest assay, these constructs have been assayed in the more sensitive transcriptional assay for activation of a fuslp-HIS3 gene. In both of these assays, the GPA$_{41}$-Gαs hybrid couples less well than the GPA$_{41}$-i2, -i3, and -16 hybrids, while the GPA$_{41}$-o$_a$, and -o$_b$ hybrids do not function in either assay.

Several predictive algorithms indicate that the amino terminal domain up to the highly conserved sequence motif LLLLGAGESG (SEQ ID NO:3) (the first L in this motif is residue 43 in GPA1) forms a helical structure with amphipathic character. Assuming that a heptahelical repeat unit, the following hybrids between yeast GPA1 and mammalian GαS can be used to define the number of helical repeats in this motif necessary for hybrid function:

GPA1-7/Gαs8-394

GPA1-14/Gαs15-394

GPA1-21/Gαs22-394

GPA1-28/Gαs29-394

GPA1-35/Gαs36-394

GPA1-42/Gαs43-394

In these hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover" hybrids of this class are those that are aligned on the first putative heptad repeat beginning with residue G11 in GPA1. In these hybrids, helical repeats are swapped from GPA1 into a GaS backbone one heptad repeat unit at a time.

GαS1-10/GPA11-17/Gαs18-394

GαS1-17/GPA18-24/GαS25-394

GαS1-17/GPA25-31/GαS32-394

GαS1-17/GPA32-38/GαS39-394

The gap that is introduced between residues 9 and 10 in the GαS sequence is to preserve the alignment of the LLLLGAGE (SEQ IG NO:4) sequence motif. This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas et al. supra). In this model, the a and d positions of the heptad repeat abcdefg are found to be conserved hydrophobic residues that define one face of the helix, while the e and g positions define the charged face of the helix. In this class of hybrids, the sequence of the GαS parent is maintained except for specific substitutions at one or more of the following critical residues to render the different helical faces of Gαs more "GPA1-like"

K8Q

+I-10

E10G

Q12E

R13S

N14D

E15P

E15F

K17L

E21R

K28Q

K32L,

V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series of junctional primers spanning different junctional points can be mixed with the outside primers to make a series of molecules each with different amounts of GPA1 and GαS sequences, respectively.

ii. GPA$_{ID}$ and GPA$_{LW}$ Hybrids.

The regions of high homology among Gβγ subunits that have been identified by sequence alignment are interspersed throughout the molecule. The G1 region containing the highly conserved GSGESGDST (SEQ ID NO:5) motif is followed immediately by a region of very low sequence conservation, the "i1" or insert 1 region. Both sequence and length vary considerably among the i1 regions of the Gα subunits. By aligning the sequences of Gα subunits, the conserved regions bounding the i1 region were identified and two additional classes of GPA1-Gα hybrids were constructed. The GPA$_{ID}$ hybrids encode the amino terminal 102 residues of GPA1 (up to the sequence QARKLGIQ) (SEQ ID NO:6) fused in frame to mammalian Gα subunits, while the GPA$_{LW}$ hybrids encode the amino terminal 244 residues of GPA1 (up to the sequence LIHEDIAKA (SEQ ID NO:7) in GPA1). The reason for constructing the GPA$_{ID}$ and GPA$_{LW}$ hybrids was to test the hypothesis that the i1 region of GPA1 is required for mediating the interaction of GPA1 with yeast Gβγ subunits, for the stable expression of the hybrid molecules, or for function of the hybrid molecules. The GPA$_{ID}$ hybrids contain the amino terminal domain of GPA1 fused to the i1 domain of mammalian subunits, and therefore do not contain the GPA1 i1 region, while the GPA$_{LW}$ hybrids contain the amino terminal 244 residues of GPA1 including the entire i1 region (as defined by sequence alignments). Hybrids of both GPA$_{ID}$ and GPA$_{LW}$ classes were constructed for GαS, C-αi2, Gαi3, Gαo$_a$, and Gα16, none of these hybrids complemented the gpa1 growth arrest phenotype.

Subsequent to the construction and testing of the GPA$_{ID}$ and GPA$_{LW}$ classes of hybrids, the crystal structures of G$_{transducin}$ in both the GDP and GTPγS-liganded form, and the crystal structure of several Gαi1 variants in the GCTPγS-liganded and GDP-AlF$_4$ forms were reported (Noel et al. supra; Lambright et al. and Coleman et al.(1994) *Science* 265:1405–1412). The crystal structures reveal that the i1 region defined by sequence alignment has a conserved structure that is comprised of six alpha helices in a rigid array, and that the junctions chosen for the construction of the GPA$_{ID}$ and GPA$_{LW}$ hybrids were not compatible with conservation of the structural features of the i1 region observed in the crystals. The junction chosen for the GPA$_{ID}$ hybrids falls in the center of the long αA helix; chimerization of this helix in all likelihood destabilizes it and the protein structure in general. The same is true of the junction chosen for the GPA$_{LW}$ hybrids in which the crossover point between GPA1 and the mammalian Gα subunit falls at the end of the short αC helix and therefore may distort it and destabilize the protein.

The failure of the GPA$_{ID}$ and GPA$_{LW}$ hybrids is predicted to be due to disruption of critical structural elements in the i1 region as discussed above. Based upon new alignments and the data presented in Noel et al (supra) Lambright et al (supra), and Coleman et al (supra) this problem can be averted with the ras-like core domain and the i1 helical domain are introduced outside of known structural elements like alpha-helices.

Hybrid A GαS1-67/GPA66-299/GαS203-394

This hybrid contains the entire i1 insert of GPA1 interposed into the GαS sequence.

Hybrid B GPA1-41/GαS4443-67/GPA66-299/GαS203-394

This hybrid contains the amino terminal 41 residues of GPA1 in place of the 42 amino terminal residues of GαS found in Hybrid A.

iii. Gαs Hybrids.

There is evidence that the "switch region" encoded by residues 171–237 of Gα transducin (using the numbering of (Noel et al (supra)) also plays a role in Gβγ coupling. First, the G226A mutation in GαS prevents the GTP-induced conformational change that occurs with exchange of GDP for GTP upon receptor activation by ligand. This residue maps to the highly conserved sequence DVGGQ (SEQ ID NO:8), present in all Gα subunits and is involved in GTP hydrolysis. In both the Gαt and Gα i1 crystal structures, this sequence motif resides in the loop that connects the β3' sheet and the α2 helix in the guanine nucleotide binding core. In addition to blocking the conformational change that occurs upon GTP binding this mutation also prevents dissociation of GTP-ligainded Gαs from Gβγ. Second, crosslinking data reveals that a highly conserved cysteine residue in the α2 helix (C215 in Gαo, C210 in Gαt) can be crosslinked to the carboxy terminal recgion of Gβ subunits. Finally, genetic evidence (Whiteway et al. (1993) *Mol Cell Biol.* 14:3233–3239) identifies an important single residue in GPA1 (E307) in the β2 sheet of the core structure that may be in direct contact with βγ. A mutation in the GPA1 protein at this position suppresses the constitutive signaling phenotype of a variety of STE4 (Gβ) dominant negative mutations that are also known to be defective in Gα-Gβγ association (as assessed in two-hybrid assay in yeast as well as by more conventional genetic tests).

The GPA1 switch region suppresses coupling to yeast Gβγ (SGS), while in the context of the GPA1 amino terminus the GPA1 switch region stabilizes coupling with Gβγ (GPβγ-SGS). This suggests that these two regions of GPA1 collaborate to allow interactions between Gα subunits and Gβγ subunits. This conclusion is somewhat mitigated by the observation that the GPA$_{41}$-Gαs hybrid that does not contain the GPA1 switch region is able to complement the growth arrest phenotype of gpa1 strains.

The role of the surface-exposed residues of this region may be crucial for effective coupling to yeast Gβγ, and can be incorporated into hybrid molecules as follows below.

GαS-GPA-Switch GαS 1-202/GPA298-350/GαS 253-394

This hybrid encodes the entire switch region of GPA 1 in the context of GαS.

GαS-GPA-α2 GQS 1-226/GPA322-332/GQS 238-394

This hybrid encodes the a$_2$ helix of GPA1 in the context of GαS.

GPA41-GαS-GPA-α2GPA1-41/GQS43-226/GPA322-332/GQS23 8-394

This hybrid encodes the 41 residue amino terminal domain of GPA1 and the α2 helix of GPA1 in the context of GαS.

In addition, hybrids that alter the surface exposed residues of the β2 and β3 sheets of αS so that they resemble those of the GPA1 QS helix can be made. These altered α2 helical domains have the following structure. (The positions of the altered residues correspond to GαS.)

L203K

K211F

D215G

K216S

D229S

These single mutations can be engineered into a GαS backbone singly and in pairwise combinations. In addition, they can be introduced in the context of both the full length GαS and the GPA$_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and co-workers (Whiteway et al (supra) that define site(s) that interact with GPA1).

In summary, the identification of hybrid Gα subunits that couple to the yeast pheromone pathway has led to the following general observations. First, GPA$_{BAM1}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a GPA1 containing GPA1-$_{41}$ could also feature the L203K mutation.

While, for the sake of simplicity, hybrids of yeast GPA1 and a mammalian Gαs have been described here, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

iv. Expression of Gα

Kang et al. supra reported that several classes of native mammalian Gα subunits were able to interact functionally with yeast α subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not preferred for uses like those described in this application. Reconstruction of G protein-coupled receptor signal transduction in yeast requires the signaling component of the heterotrimeric complex (Gβγ) to be present stoichiometrically with Gα subunits. An excess of Gα subunits (as was required for coupling of mammalian Gαi2 and Gαo to yeast Gβγ in Kang et al.) would dampen the signal in systems where Gβγ subunits transduce the signal. An excess of Gα subunits raises the background level of signaling in the system. Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpa1 genotype when expressed from the GPA1 promoter on low copy plasmids or from an integrated, single copy gene. In the work described in this application heterologous Gα subunits have been assayed in two biological systems. In the first assay heterologous Gα subunits are tested for an ability to functionally complement the growth arrest phenotype of gpa1 strains. In the second assay the transcription of a fus1-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

D. Chimeric Yeast βγ Subunits

In addition to or in place of modifying G protein Gα subunits, yeast or heterologous Gβ or Gγ subunits can be modified. The methods described above with regard to Gα modification can be used to alter either or both of these subunits as well. For example, alignments of the yeast sequence and heterologous sequences can be made and combined with information regarding important functional domains. Such information can then be used to provide guidance in making mutations in yeast or heterologous sequences. Likewise, chimeric Gβ or Gγ molecules can be constructed to enhance the coupling of heterologous GPCRs to a yeast pheromone signaling pathway.

The yeast STE4 and STE18 are related to the metazoan G protein β and γ subunits, respectively (Whiteway et al. 1989. Cell. 56:467). The β and γ subunits must be capable of interaction with one another as well as with the α subunit and with the effector. Previous work has suggested that mammalian β or γ subunits are divergent enough from their yeast homologues that they cannot functionally replace STE4 or STE 18. (Coria et al. 1996. Yeast. 12:41). Thus, in preferred embodiments, modifications are made to heterologous Gβ or Gγ subunits expressed in yeast and/or chimeric subunits are made to enhance heterologous receptor coupling.

The primary structure of G-protein β subunits is highly conserved from yeast to humans; Ste4 shares approximately 40% identity with human Gβ isoforms (Leberer et al. 1992 EMBO Journal 11:4085). STE 4 and the Gβs are 420, and 340 or 341 amino acids long, respectively, and belong to the family of proteins with WD-40 motifs (van der Voorn and Ploegh. 1992. FEBs Lett. 307:131). These motifs can be used to divide Gβ and STE4 into eight blocks (Coria et al. Yeast 1996. 12:41). Among the mammalian Gβs, some have been found to exhibit Gγ subunit selectivity (Pronin and Gautham. 1992. Proc. Natl. Acad. Sci. USA 89:6220; Schmidt et al. 1992. J. Biol. Chem. 267:13807; Kleuss et al. 1992. Nature. 358:424). An alignment of the metazoan and yeast G protein β subunits is provided by Corai et al. (1996. Yeast. 12:41). Such an alignment can be used to provide guidance for making mutations to G protein β subunits as described for Gα above. In addition, certain regions of STE4 have been found to be important and thus, may be less amenable to manipulation than other portions of the polypeptide. For example, the c-terminus of the STE4 product is essential for downstream signaling (Coria et al. 1995. FEBS Letters 367:122). Mutations to two small regions in the amino terminal half of Ste4 have also been shown to inhibit signaling (Leberer et al. supra). Mutations which influence the interaction of STE4 and GPA1 have also been identified; mutations to the second copy of the WD40 repeat can be modified to reduce the interaction between STE4 and GPA1, without influencing other aspects of STE4 function (Whiteway et al. 1994. Mol. Cell. Biol. 14:3223).

The Gγs, including STE18, diverge more strongly from each other than do the Gβs. Even among the mammalian G protein γ subunits, there is a fair amount of divergence. The γ subunit may determine the functional specificity of the βγ subunit complex. Complete cDNAs for the γ1 subunit from bovine retina (Hurley et al. Proc. Nat'l Acad. Sci USA. 1984. 81:6948) the γ1, γ3, and γ7 subunits from bovine brain (Robishaw et al. J. Biol. Chem. 1989. 264:15758; Gautam et al. Science. 1989. 244:971; Gautam et al. Proc. Nat'l Acad. Sci. USA. 1990 87:7973; Cali et al. J. Biol. Chem. 1992. 267:24023), and the γ5 subunit from bovine and rat liver (Gisher et al. 1992. 12:1585) have been reported.

The STE18 gene of yeast terminates with a CAAX box (where A is an aliphatic amino acid, and X is any uncharged amino acid). This sequence is involved in prenylation of Gγ and is likely important in the localization of Gγ to the membrane and may, thus, be less amenable to manipulation than other portions of the sequence. (Kurjan. 1992. Ann. Rev. Biochem. 61:1097). Saturation mutagenesis has also provided insight into regions of STE18 that are important in STE18 function. Mutations in STE18 which compensate for mutations in STE4 were identified at serine 65, threonine 71 and valine 80. Dominant negative alleles of the STE18 gene were also identified (Whiteway et al. 1992. Biochem. Cell. Biol. 70:1230). These truncated proteins were found to lack the carboxyl terminus of STE 18, including the CAAX box (Whiteway et al. supra).

An alignment of yeast Gγ, STE18, and mammalian Gγs can be made as indicated for the other G protein subunits. Such an alignment can be used in constructing mutant Gγ subunits or chimeric Gγ subunits. In preferred embodiments, mammalian Cγ2 is used in making G protein γ subunit chimeras.

VIII. Leader Sequences

It has been demonstrated that most of the mammalian extracellular, secreted proteins are poorly secreted when expressed in yeast. However, in many cases their secretion levels are markedly increased when their native signal sequences are replaced by the signal sequences of yeast proteins that interact more efficiently with the ER translocation complex. Specifically, the signal sequences of yeast invertase and acid phosphatase have been widely used in biotechnology to direct the secretory expression of the heterologous proteins. However, it is well established that even though many foreign proteins are targeted to the ER by the yeast signal sequences, not all of them advance further in the secretory pathway. The major problem appears to be in the malfolding and/or improper glycosylation of the heterologous proteins that results in their retention in the ER by the quality control apparatus of the yeast cell.

In many cases, the leader sequence of a precursor of yeast mating pheromone, α-factor, has been used successfully to overcome this problem (Brake, A. J. (1989) in *Yeast Genetic Engineering* (Barr, P. J., Brake, A. J., and Valenzuela, P., eds) pp. 269–280, Butterworths, London; Brake, A. J. (1990) *Meth. Enzymol.* 185, 408–441, and references cited therein). This sequence, in addition to the N-terminal signal peptide of 17 residues, includes a hydrophilic pro-region which contains 72 residues and bears three sites of N-linked glycosylation. The pro-region is extensively glycosylated in the ER and Golgi and is cleaved by Kex2 endopeptidase in the late Golgi compartment. The presence of the pro-region at the N-terminus has been demonstrated to promote transport of heterologous proteins from the ER to the periplasm. It is likely that the pro-region can somehow facilitate correct protein folding. Alternatively, it may be recognized by the quality control apparatus as a properly folded structural unit thus allowing an entire fusion protein to leave the ER.

The invertase leader can also be used. This leader sequence has been demonstrated to be cleaved from nascent invertase peptide, or nascent heterologous peptide, in the course of translocation into the endoplasmic reticulum.

A. Peptide Expression

In certain embodiments, such a leader sequence can be used to express a peptide library of the present invention. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides may either undergo re-uptake into the cell, transit through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless. these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion of peptides, or, if such secretion is provided, any particular secretion signal or transport pathway. In certain embodiments, peptides expressed with a signal sequence may bind to and activate receptors prior to their transport to the cell surface.

B. GPCR Expression

In other embodiments, a leader sequence of a yeast secreted protein can be used to direct transport of receptors, for example, G-protein coupled receptors to the plasma membrane as described in detail in the appended examples. Previous work has demonstrated the expression of foreign, secreted proteins in yeast cells using the α-factor leader. However, when a heterologous membrane bound receptor, the rat M5 receptor, was expressed using such a system, it was found that the heterologous GPCR did not functionally integrate into the yeast cell signaling pathway (Huang et al. *Biochem. and Biophys. Res. Comm.* 1992. 182:1180). The transport of both secreted_ and transmembrane proteins into the endoplasmic reticulum in yeast is promoted by the same protein translocation complex, including the Sec61, Sec62 and Sec63 proteins. All the secreted proteins possess a signal sequence at their N-termini which is recognized by the translocation complex and serves as an ER targeting signal. A typical signal sequence is comprised of several positively charged residues at the N-terminus followed by a hydrophobic core and a C-terminal site of processing by signal peptidase. Some transmembrane proteins, for example, metabotropic glutamate receptors and vasoactive intestinal polypeptide receptors, also possess the N-terminal signal sequences, whereas some do not. In the latter case, a first transmembrane domain is believed to interact with the ER translocation machinery. The use of the α-factor leader sequence may, therefore, be particularly desirable for functional expression of certain receptors.

In certain embodiments, it will be desirable to further modify the yeast cells of the present invention. For example, in one embodiment it will be desirable to disrupt the yeast calnexin-like gene, CNE1, to improve receptor transport from the endoplasmic reticulum to the Golgi. In yet other embodiments, it will be desirable to overexpress the gene encoding Ast1, to increase transport form the Golgi to the plasma membrane. In yet other embodiments, it will be desirable to disrupt END3 and/or END4, to inhibit or prevent receptor internalization. Additionally or alternatively, the CHC1 gene (clathrin-encoding) can be disrupted to inhibit or prevent receptor internalization. In another embodiment, it may be desirable to disrupt the MVP-1 gene to inhibit or prevent transport from the Golgi to the prevacuolar compartment.

In preferred embodiments, certain heterologous receptors are expressed using a leader sequence other than an α factor leader sequence.

IX. Test Compounds

Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261:1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422. Horwell et al. 1996 Immunopharmacology 33:68; and in Gallop et al. 1994. J. Med. Chem. 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention. The contents of each of these applications is expressly incorporated herein by this reference.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990)*Science* 249:404–406); (Cwirla et al. (1990) *Proc. Natl. Acad. Sci.* 87:6378–6382); (Felici (1991) *J. Mol. Biol.* 222:301–310); (Ladner supra).

In certain embodiments, the test compounds are exogenously added to the yeast cells expressing a recombinant receptor and compounds that modulate signal transduction via the receptor are selected. In other embodiments, the yeast cells express the compounds to be tested. For example, a culture of the subject yeast cells can be further modified to collectively express a peptide library as described in more detail in PCT Publication WO 94/23025 the contents of which is expressly incorporated herein by this reference.

Other types of peptide libraries may also be expressed, see, for example, U.S. Pat. Nos. 5,270,181 and 5,292,646; and PCT publication WO094/02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

Autocrine Yeast Cells

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. For example, peptide libraries are systems which simultaneously display, in a form which permits interaction with a target, a highly diverse and numerous collection of peptides. These peptides may be presented in solution (Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409). plasmids (Cull et al. (1992) *Proc Natl Acad Sci USA* 89:1865–1869) or on phage (Scott and Smith (1990) *Science* 249:386–390): (Devlin (1990)*Science* 249:404–406); (Cwirla et al. (1990) *Proc. Natl. Acad. Sci.* 87:6378–6382); (Felici (1991) *J. Mol. Biol.* 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Ser. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.*(1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, (U.S. Pat. Nos. 5,270,181 and 5,292,646; and PCT publication WO94/02502). The combinatorial peptide can be attached one the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists. For example, the surrogate ligand can be mutagenized to generate a library of peptides with some relationship to the original peptide. This library can be expressed in a reagent cell of the present invention, and other receptor activators can be isolated from the library. This may permit the identification of even more potent surrogate ligands.

In still another embodiment, the combinatorial polypeptides are produced from a cDNA library.

In a preferred embodiment of the present invention, the yeast cells collectively produce a "peptide library", preferably including at least 103 to 107 different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

In embodiments in which the test compounds it may be desirable to express such peptides in the context of a leader sequence. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention. The present invention does not require periplasmic secretion, or, if such secretion is provided, any particular secretion signal or transport pathway.

X. Screening and Selection: Assays of Second Messenger Generation

When screening for bioactivity of compounds, intracellular second messenger generation can be measured directly. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{++}$ transients, as well as stimulating cardiac $K^+$ channels.

In one embodiment, the GTPase enzymatic activity by G proteins can be measured in plasma membrane preparations by determining the breakdown of $\gamma^{32}P$ GTP using techniques that are known in the art (For example, see *Signal Transduction. A Practical Approach.* G. Milligan. Ed. Oxford University Press, Oxford England). When receptors that modulate cAMP are tested, it will be possible to use standard techniques for cAMP detection, such as competitive assays which quantitate [$^3H$]cAMP in the presence of unlabelled cAMP.

Certain receptors stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) *Environ Health Perspect* 94:45–56). As an exemplary method of Ca++ detection, cells could be loaded with the Ca++ sensitive fluorescent dye fura-2 or indo-1, using standard methods, and any change in Ca++ measured using a fluorometer.

The other product of PIP2 breakdowns DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) *Proc. Natl. Acad. Sci. USA* 81:7426–7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 genes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

Modified methods for detecting receptor-mediated signal transduction exist and one of skill in the art will recognize suitable methods that may be used to substitute for the example methods listed.

In one embodiment, the indicator gene can be used for detection. In one embodiment an indicator gene is an unmodified endogenous gene. For example, the instant method can rely on detecting the transcriptional level of such pheromone system pathway responsive endogenous genes as the Bar1 or Fus1, Fus 2, mating factor, Ste3 Ste13, Kex1, Ste2, Ste6, Ste7, sSst2, or Chs1. (Appletauer and Zchstetter. 1989. Eur. J. Biochem. 181:243).

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. The previous discussion of mutations with regard to G proteins and G protein coupled receptors is reiterated here.

For example, in the case of the Bar1 gene, the promoter of the gene can be modified to enhance the transcription of Bar1 upon activation of the yeast pheromone system pathway. Bar1 gene transcription is inactivated upon exposure of yeast cells to mating factor. The sequence of the Bar1 gene is known in the art (see e.g., U.S. Pat. No. 4,613,572). Moreover, the sequences required for α-factor-enhanced expression of the Bar1 and other pheromone responsive genes have been identified. (Appeltauer and Achstetter 1989. Eur. J. Biochem. 181:243; Hagen et al. 1991. Mol. Cell. Biol. 11:2952). In an exemplary embodiment, the yeast Bur1 promoter can be engineered by mutagenesis to be more responsive. e.g., to more strongly promoter gene transcription, upon stimulation of the yeast pheromone pathway. Standard techniques for mutagenizing the promoter can be used. In such embodiments, it is desirable that the conserved oligonucleotide motif described by Appeltaure et al. be conserved.

In yet other embodiments, rather than measuring second messenger production or alterations in transcription, the activity of endogenous yeast proteins can be assayed. For example, in one embodiment, the signal transduction pathway of the receptor upregulates expression or otherwise activates an enzyme which is capable of modifying a substrate which can be added to the cell. The signal can be detected by using a detectable substrate, in which case loss of the substrate signal is monitored, or alternatively, by using, a substrate which produces a detectable product. In certain embodiments, the substrate is naturally occurring. Alternatively, the substrate can be non-naturally occurring. In preferred embodiments, BAR1 activity can be measured.

In other embodiments, the modulation of a receptor by a test compound can result in a change in the transcription of a gene, which is not normally pheromone responsive. In preferred embodiments, the gene is easily detectable. For example, in a preferred embodiment, the subject assay can be used to measure Pho5, a secreted acid phosphatase. Acid phosphatase activity can be measured using standard techniques.

In other embodiments, reporter gene constructs can be used. Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art. Reporter genes include any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737), bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368) and green fluorescent protein (U.S. Pat. No. 5,491,084; WO96/23898).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP. nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum, Changelian et al. (1989). Proc. Natl. Acad. Sci. 86:377–381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

In certain embodiments, when searching for compounds which can function as agonists of G protein-coupled receptors, or other pheromone system proteins, the growth arrest consequent to activation of the pheromone response pathway is an undesirable effect since cells that bind agonists stop growing while surrounding cells that fail to bind agonists will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter and applying selective conditions).

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA-binding repressor protein, and incorporating a suitable operator site into the promoter or other suitable region of the marker gene.

In the case of yeast, exemplary positively selectable (beneficial) genes include the following: URA3, LYS2, HIS3, LEU2, TRP1; ADE1,2,3,4,5,7,8; ARG1, 3, 4, 5, 6, 8; HIS1, 4, 5; ILV1, 2, 5, THR1, 4; TRP2, 3, 4, 5; LEU1, 4; MET2,3,4,8,9,14,16,19; URA1,2,4,5,10; H0M3,6; ASP3; CHO1; ARO 2,7; CYS3; OLE1; IN01,2,4; PR01,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In another version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase, inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanin), and other recessive drug-resistant markers.

In one example, the reporter gene effects yeast cell growth. The natural response to signal transduction via the yeast pheromone system response pathway is for cells to undergo growth arrest. This is a preferred way to select for antagonists of a ligand/receptor pair that stimulates a the pathway. An antagonist would inhibit the activation of the pathway; hence, the cell would be able to grow. Thus, the FAR1 gene may be considered an endogenous counterselectable marker. The FAR1 gene is preferably inactivated when screening for agonist activity.

The reporter gene may also be a screenable gene. The screened characteristic may be a change in cell morphology, metabolism or other screenable features. Suitable markers include beta-galactosidase (Xgal, $C_{12}FDG$, Salmon-gal, Magenta-Gal (latter two from Biosynth Ag)), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xga1 into a blue pigment. Again, the promoter may be receptor-induced or receptor-inhibited.

XI. Other Optional Alterations to Yeast Cells

The choice of appropriate host cell will also be influenced by the choice of detection signal. For instance, reporter constructs can provide a selectable or screenable trait upon transcriptional activation (or inactivation) in response to a signal transduction pathway coupled to the target receptor. The indicator gene may be an unmodified gene already in the host cell pathway, such as the genes responsible for growth arrest in yeast. In certain embodiments a host cell gene may be operably linked to a "receptor-responsive" promoter. Alternatively, it may be a heterologous gene that has been so linked. Suitable genes and promoters are discussed below.

To achieve optimal selection or screening, the host cell phenotype will be considered. For example, introducing a pheromone-responsive chimeric HIS3 gene into a yeast that has a wild-type HIS3 gene would frustrate genetic selection. Thus, to achieve nutritional selection, an auxotrophic strain is preferred. Yeast strains that are auxotrophic for histidine (HIS3) are known, see Struhl and Hill, (1987) *Mol. Cell. Biol.*, 7:104; Fasullo and Davis, *Mol. Cell. Biol.*, (1988) 8:4370. The HIS3 (imidazoleglycerol phosphate dehydratase) gene has been used as a selective marker in yeast. See Sikorski and Heiter, (1989) Genetics. 122:19; Struhl, et al., P.N.A.S. (1979) 76:1035: and, for FUS1-HIS3 fusions, see Stevenson, et al., (1992) *Genes Dev.*, 6:1293.

In certain embodiments, the host yeast cell can be modified in other ways. For example, it may be desirable to inactivate, such as by mutation or deletion, a homologous receptor, e.g. a pheromone receptor, present in the cell in order to minimize interference with signaling via the heterologous receptor. "Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

In a preferred embodiment of the subject assay, the yeast cells possess one or more of the following characteristics: (a) the endogenous FUS1 gene has been inactivated; (b) the endogenous SST2 gene, and/or other genes involved in desensitization, have been inactivated, (c) if there is a homologous, endogenous receptor gene it has been inactivated; and (d) if the yeast produces an endogenous ligand to the exogenous receptor, the genes encoding for the ligand been inactivated.

It is desirable that the exogenous receptor be exposed on a continuing basis to the peptides. In some instances, this may result in desensitization of the pheromone pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1, bar1, ste2, ste3, pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

In certain embodiments, it will be desirable to complement the host yeast cells, e.g., least partial function of an inactivated gene of the host cell can be supplied by an exogenous nucleic acid. For instance, yeast cells can be "mammalianized", and even "humanized", by complementation of receptor and signal transduction proteins with mammalian homologues. To illustrate, inactivation of a yeast Byr2/Ste11 gene can be complemented by expression of a human MEKK gene.

Complementations for use in the subject assay can be constructed without any undue experimentation. Indeed, many yeast genetic complementations with mammalian signal transduction proteins have been described in the art. For example, Mosteller et al. (1994) Mol Cell Biol 14:1104–12 demonstrates that human Ras proteins can complement loss of ras mutations in *S. cerevisiae*. Moreover, Toda et al. (1986) Princess Takamatsu Symp 17: 253–60 have shown that human ras proteins can complement the loss of RAS1 and RAS2 proteins in yeast, and hence are functionally homologous. Both human and yeast RAS proteins can stimulate the magnesium and guanine nucteotide-dependent adenylate cyclase activity present in yeast membranes. Ballester et al. (1989) Cell 59: 681–6 describe a vector to express the mammalian GAP protein in the yeast *S. cerevisiae*. When expressed in yeast GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151: 279–84 describes that a human Ras-specific guanine nucleotide-exchange factor Cdc25GEF can complement the loss of CDC25 function in *S. cerevisiae*. Martegani et al. (1992) EMBO J 11: 2151–7 describe the cloning by functional complementation of a mouse cDNA encoding a homolog of CDC25, a *Saccharomyces cerevisiae* RAS activator. Vojtek et al. (1993) J Cell Sci 105: 777–85 and Matviw et al. (1992) Mol Cell Biol 12: 5033–40 describe how a mouse CAP protein, e.g., an adenylyl cyclase associated protein associated with ras-mediated signal transduction, can complements defects in *S. cerevisiae*. Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364: 349–52 describe the complementation of byr1 in fission yeast by mammalian MAP kinase kinase (MEK). Parissenti et al. (1993) Mol Cell Endocrinol 98: 9–16 describes the reconstitution of bovine protein kinase C (PKC) in yeast. The Ca(2+) and phospholipid-dependent Ser/Thr kinase PKC plays important roles in the transduction of cellular signals in mammalian cells. Marcus et al. (1995) PNAS 92: 6180–4 suggests the complementation of shk1 null mutations in *S. pombe* by the either the structurally related *S. cerevisiae* Ste20 or mammalian p65PAK protein kinases.

XII. Pharmaceutical Preparations of Identified Compounds

After identifying certain test compounds as potential surrogate ligands, or receptor antagonists, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

All patents, published patent applications and other references disclosed herein are hereby expressly incorporated by reference. In addition the contents of U.S. Ser. No.: 08/322,137 (now U.S. Pat. No. 6,100,042, issued Aug. 8, 2000); U.S. Ser. No. 08/463,181 abandoned and U.S. Ser. No. 08/946,298 are hereby incorporated by this reference.

EXEMPLIFICATION

The invention now being generally described will be more readily understood by reference to the following examples, which are included merely for purposes of illustration of certain aspects and embodiments of the present invention and are not intended to limit the invention.

Example 1
Construction of stp22 Mutant Strains

The genotypes of *S. cerevisiae* strains used in the present study are shown in Table 1.

TABLE 1

Saccharomyces cerevisiac strains.

| Strain | Genotype |
|---|---|
| CY2120 | MATα sst2-2 gpal-1163 far1-1442 FUS1p-HIS3 tbt1-1 can1 stel4::trpl::LYS2 ste3-1156 lys2 ura3 leu2 trpl his3 |
| CY8342 | MATα GPA1p-GαsE10K far1-1442 FUS1p-HIS3 tbt1-1 can1 ste14::trpl::LYS2 ste3-1156 lys2 ura3 leu2 trp1 his 3 |
| CY8350 | MATα GPA1p-GαsD229S far1-1442 FUS1p-HIS3 tbt1-1 can1 ste14::trpl::LYS2 ste3-1156 lys2 ura3 leu2 trp1 his3 |
| CY9434 | MATα GPA1p-Gαi2 STE18-γ6-3841 far1-1442 FUS1-p-HIS3 tbt-1 can1 ste14::trp1::LYS2 ste3-1156 lys2 ura3 leu2 trp1 his3 |
| CY9436 | MATα GPA1p-Gαi2 STE18-γ10-3843 far1-1442 FUS1p-H1S3 tbt-1 stel4::trp1::LYS2 ste3-1156 lys2 ura3 leu2 trp1 his3 |
| CY9438 | MATα STE18-γ6-3841 far1-1442 FUS1p-HIS3 tbt1-1 can1 stel4::trpl::LYS2 ste3-1156 lys2 ura3 leu2 trpl his3 |
| CY10150 | MATα GPA1p-GαsD229S STE18-γ6-3841 far1-1442 FUS1p-HIS3 tbt1-1 can1 ste14::trp1::LYS2 ste3-1156 lys2 ura3 leu2 trpl his3 ade2-3447 ade8-3457 |
| CY10517 | MATα GPA1p-GαsE10K STE18-γ6-3841 far1-1442 FUS1p-HIS3 tbt1-1 can1 ste14::trp1::LYS2 ste3-1156 lys2 ura3 leu2 trpl his3 ade2-3447 ade8-3457 |
| CY10796 | MATα stp22::TRP1 STE18-γ6-3841 far1-1442 FUS1p-HIS3 tbt1-1 can1 ste14::trp1::LYS2 ste3-1156 lys2 ura3 leu2 trp1 his3 |
| CY10981 | MATα sst2-2 far1-1442 FUSIp-HIS3 tbt1-1 can1 ste14::trp1::LYS2 ste3-1156 lys2 ura3 leu2 trp1 his3 |
| CY11699 | MATα stp22::TRP1 sst2-2 gpa1-1163 far1-1442 FUS1p-HIS3 tbt1-1 can1 ste14::trp1::LYS2 ste3-1156 lys2 ura3 leu2 trp1 his3 |
| CY11701 | MATα stp22::TRP1 GPA1-Gαi2 STE18-γ6-3841 far1-1442 FUS1p-HIS3 tbt1-1 can1 ste14::trp1::LYS2 ste3-1156 lys2 ura3 leu2 trp1 his3 |
| CY11702 | MATα stp22::TRP1 GPA1-Gαi2 STE18-γl0-3843 far1-1442 FUS1p-HIS3 tbt1-1 can1 ste14::trp1::LYS2 ste3-1156 lys2 ura3 leu2 trp1 his3 |
| CY11718 | MATα stp22::TRP1 sst2-2 farl-1442 FUS1p-HIS3 tbt1-1 can1 ste14::trp1::LYS2 ste3-1156 lys2 ura3 leu2 trp1 his3 |
| CY12201 | MATα stp22::hisG STE18-γ6-3841 far1-1442 FUS1p-HIS3 tb1-1 can1 ste14::trp1::LYS2 ste3-1156 lys2 urae leu2 trp1 his 3 |
| CY12023 | MATα stp22::TRP1 GPA1p-GαsE10K far1-1442 FUS1p-HIS3 tbt1-1 can1 ste14::trp1::LYS2 ste3-1156 lys2 ura3 leu2 trp1 his 3 |
| CY12024 | MATα stp22::TRP1 GPA1p-GαsD229S far1-1442 FUS1p-HIS3 tbt1-1 can1 ste14::trp1::LYS2 ste3-1156 lys2 ura3 leu2 trp1 his3 |
| CY12025 | MATα stp22C::TRP1 GPA1p-GαsD229S STE18-γ6-3841 far1-1442 FUS1p-HIS3 tbt1-1 can1 ste14::trp1::LYS2 ste3-1156 lys2 ura3 leu2 trp1 his3 ade2-3447 ade8-3457 |
| CY12026 | MATα stp22::TRP1 GPA1p-GαsE10K STE18-γ6-3841 far1-1442 FUS1p-HIS3 tbt1-1 can1 ste14::trp1::LYS2 ste3-1156 lys2 ura3 leu2 trp1 his3 ade2-3447 ade8-3457 |
| CY12357 | MATα stp22::hisG sst2-2 far1-1442 FUS1p-HIS3 tbt1-1 can1 ste14::trpl::LYS2 ste3-1156 lys2 ura3 leu2 trp1 his3 |

A plasmid pDJ225 (Cp4298) designed to disrupt (i.e., "knockout") the STP22 gene was kindly provided by Dr. D. Jenness. The complete sequence of the STP22 gene is publicly available on GenBank (Accession Number AF004731). An alternative STP22 knockout plasmid that allows excision of a genetic marker URA3 from the chromosome of the knockout mutants was constructed as follows. The plasmid Cp4298 bearing stp22::TRP1 fragment was digested with XbaI, blunt-ended using Klenow fragment and ligated with synthetic Bgl II linker (5'-CCAGATCTGG-3') SEQ ID NO:9). As a result a plasmid Cp4588 was constructed. This vector was digested with Bgl II and ligated with a 4.1-kb fragment containing yeast URA3 gene flanked by hisG repeats. This gave rise to the plasmid Cp4748 containing STP22 gene disrupted with hisG-URA3-hisG cassette. The characteristics of other yeast vectors employed are listed in Table 2.

TABLE 2

Saccharomyces cerevisiae expression vectors.

| Vector | Genetic markers |
|---|---|
| Cp1947 | FUS1p-lacZ URA3 2 micron-ori REP3 Amp$^R$ |
| Cp3390 | GPA1p-rGαD229S TRP1 CEN6 ARS4 Amp$^R$ |
| Cp3776 | PGKp-hSSTR2 LEU2 2 micron-ori REP3 Amp$^R$ |
| Cp3924 | PGKp-hNocR LEU2 2 micron-ori REP3 Amp$^R$ |
| Cp4261 | PGKp-αF-hNocR-PHO5term LEU2 2 micron-ori REP3 Amp$^R$ |
| Cp4268 | PGKp-hSSTR2 LEU2 2 micron-ori REP3 Amp$^R$ |
| Cp4328 | PGKp-Ste2-hNocR LEU2 2 micon-ori REP3 Amp$^R$ |
| Cp4421 | PGKp-αF-hMCR4-PHO5term LEU2 2 micron-ori REP3 Amp$^R$ |
| Cp4801 | PGKp-αF-hSSTR2-PHO5term LEU2 2 micron-ori REP3 Amp$^R$ |
| Cp5038 | PGKp-αF-hMCR4-PHO5term LEU2 2 micron-ori REP3 Amp$^R$ |
| Cp5115 | PGKp-hMCR4 LEU2 2 micron-ori REP3 Amp$^R$ |
| Cp5116 | PGKp-hMCR54 LEU2 2 micron-ori REP3 Amp$^R$ |
| Cp5300 | GPA1A345T-Gαi2 TRP1 CEN6 ARS4 Amp$^R$ |
| Cp5394 | PGKp-hCRFR1 LEU2 2 micron-ori REP3 Amp$^R$ |
| Cp5396 | PGKp-hCRFR2α LEU2 2 micron-ori REP3 Amp$^R$ |

Two strains bearing stp22 knockout mutation have been constructed. First, a series of strains were made using the original knockout plasmid pDJ228 (Cp4298) supplied by D. Jenness. The plasmid was digested with SpeI and SacI and used for yeast transformation. Transformants showing tryptophan-independent growth were isolated. As a result, a stp22 mutation was introduced into the strains CY9438, CY2120, CY9434, CY9436, CY10981, CY8342, CY8350, CY10150, and CY10517. The corresponding mutant strains were designated CY10796, CY11699, CY11701. CY11702. CY11718, CY12023, CY12024, CY12025, and CY12026, respectively (Table I). All these strains bear an integrated copy of a fragment encoding Gα subunit Gpa1, Gpa1(41)-Gαi2, GαsD229S or GαsE10K. The presence of stp22 mutation was verified by PCR analysis of chromosomal DNA. Furthermore, the phenotypes of the mutant strains were confirmed by performing a test for temperature-sensitive growth as well as by measurement of secreted activity of carboxypeptidase Y (CPY). As mentioned above the stp22 mutants exhibit mild temperature sensitive growth defect and mislocalize CPY to the cell surface.

In order to allow an introduction of any Gα subunit-encoding plasmid into the stp22 background, two additional mutant strains have been made using the plasmid Cp4748 described above. The latter plasmid was digested with SarI and SpeI followed by purification of a 6-kb fragment which was used for yeast transformation. The Ura$^+$ colonies were isolated and tested for the stp22 phenotype. To allow excision of an integrated copy of URA3 genetic marker, the positive transformants were propagated in YEPD followed by plating on media supplemented with 5-fluoroorotic acid (FOA). The isolated uracil-dependent colonies were tested for stp22 phenotype. As a result, the stp22 mutants CY12201 and CY12357 were constructed (see Table I).

Example 2
Optimization of a Functional Assay for the Human Nociceptin Receptor (hNocR).

The nociceptin receptor (NocR) (ORLI, orphanin FQ receptor) represents an opioid-like receptor which transmits signal through a G protein of Gi/Go class. This protein shows substantial homology to the opioid family of receptors. However, despite of their structural similarity, the nociceptin and opioid receptors appear to play the opposite physiological roles. In fact, nociceptin, a heptadecapeptide agonist of NocR, has been shown to reverse analgesia mediated by the opioid receptors (Mogil, J., Grisel, J., Reinscheid, R. K., Civelli, O., Bellknap, J. K., and Grandy, D. K. (1996).

To determine the effect of the stp22 mutation in pheromone pathway signaling through the NocR, the isogenic strains CY10981 (wild type) and CY11718 (stp22) were transformed with the expression vectors encoding hNocR (Cp3994). Ste2-hNocR (Cp4328) (using the Ste-2 leader), Inv-hNocR (Cp4735) (using the invertase leader) or αF-hNocR (Cp4261)(using the α-factor leader), together with the plasmid Cp1947 encoding the FUS1-LacZ reporter gene, and used for β-galactosidase activity assays to determine the induction of pheromone-responsive FUS1 promoter. All the expression vectors were constructed using a DNA fragment encoding human nociceptin receptor which was PCR amplified using the following oligonucleotides: NCOI-F: 5'-CATGCCATGGAGCCCCTCTTCC-3' (SEQ ID NO:1) and XBAI-R: 5'-CATGTCTAGATTAT GCGGGCCGCGGTACC-3' (SEQ ID NO:2) and digested with NcoI and XbaI. The β-galactosidase activity assays were performed as follows: Yeast cultures were grown in SC-LU pH 6.8 medium to an $A_{600}$ of 0.75–1.0 and diluted with the same media to an $A_{600}$ of 0.3. The culture aliquots of 100 μl were incubated in a 96-well plate in the absence of in the presence of nociceptin (as the ligand) at 30° C. for 4 hours. To assay the enzyme activity, 20 μl of 0.6 M sodium phosphate, pH 7.0, 60 mM KCl, 6 mM MgCl$_2$, 1.5% β-mercaptoethanol, 2.5% Triton X-100 and 10 mM CPRG was added, followed by incubation at room temperature for 1 hour. Reactions were terminated by addition of 60 μl of 1 M sodium carbonate, followed by measurement of optical densities at 575 nm.

Alternatively, the NocR expression vectors were expressed in yeast cells carrying a FUS1-HIS3 gene. In his3 auxotroph yeast host cells, activation of the pheromone response pathway by ligand stimulation of the receptor induces the activity of the pheromone-responsive FUS1 promoter, driving expression of the HIS3 reporter gene, thereby allowing the yeast cells to grow in selective medium in the absence of histidine.

As demonstrated by sucrose density gradient centrifugation and by indirect immunofluorescence microscopy, the hNocR expressed in wildtype yeast under the control of a strong constitutive PGK promoter was localized to intracellular compartments but not to the plasma membrane. Consistent with this observation, no coupling of the native hNocR to the pheromone response pathway was detected using the ligand-spot assay as a functional test (activation of FUS1/HIS3). In these assays, 5 μl of 1 μM, 10 μM, 100 μM or 1 mM nociceptin was spotted on a lawn of yeast cultures on selective media (lacking histidine). Expression of the receptor as a fusion to either N-terminal sequence of Ste2 protein (Ste2-hNocR) or the signal sequence of invertase (Inv-hNocR) in wildtype cells did not promote receptor-mediated signaling. In contrast, the hNocR expressed as a fusion to the leader sequence of c-factor (αF-hNocR) did confer some functional coupling in the wildtype cells as judged by ligand-induced growth stimulation.

Use of an stp22 mutant strain led to a remarkable enhancement of signaling mediated by nociceptin receptor. All the receptor forms tested were shown to be functional in the stp22 background and the sensitivity of the ligand-spot assay for the α F-hNocR was increased by approximately five- to ten-fold compared with a wild type strain in which Stp22p was expressed. These data are in a good agreement with the estimated levels of FUS1-lacZ induction. All the stp22 strains bearing different expression vectors exhibited a 10–40-fold maximal increase in the levels of β-galactosidase activity in response to exogenous nociceptin. Also of note is the fact that the estimated $EC_{50}$ value for αF-hNocR was several-fold lower when receptor was expressed in stp22 background.

Example 3
Optimization of a Functional Assay for the Human Melanocortin Receptor 4 (hMCR4).

The isogenic yeast strains CY9438 (wildtype) and CY12201 (stp22) expressing rat GαsD229S were transformed with the expression vectors encoding human MCR4 (Cadus 5115) or αF-MCR4 (Cadus 4421), together with the plasmid Cp1947 encoding the FUS1-lacZ reporter gene, and used for β-galactosidase activity assays (as described in Example 2) to determine the induction of pheromone-responsive FUS1 promoter. NDP-α-MSH was used as the ligand. Alternatively, the melanocortin receptor plasmids were expressed in yeast cells carrying a FUS1-HIS3 gene and activation of FUS1-HIS3 was determined using ligand-spot assays (as described in Example 2).

As demonstrated by both ligand-spot assays and FUS1-lacZ induction assays, the native melanocortin receptor 4 (hMCR4) also promoted a considerably more robust ligand-dependent response in the stp22 background than in the wild type strain. Specific ligand-induced levels of β-galactosidase activity was increased approximately 2-fold in the stp22 mutant strain. This was accompanied by a several-fold decrease of $EC_{50}$ value for NDP-α-MSH which was used as the test ligand. In contrast, however, efficiency of signaling mediated by the α-factor fusion receptor was decreased as a result of the stp22 mutation.

Example 4
Optimization of a Functional Assay for the Human Somatostatin Receptor 3 (hSSTR3).

The isogenic yeast strains CY9438 (wildtype) and CY12201 (stp22) were transformed with the plasmids Cp4801 encoding αF-hSSTR3, Cp5300 encoding Gpa1A345T, in which five C-terminal residues were replaced with the corresponding region of human Gai2, and Cp1947 encoding the FUS1-LacZ reporter gene, and used for β-galactosidase activity assays (as described in Example 2) to determine the induction of pheromone-responsive FUS1 promoter. Somatostatin-14 was used as the ligand.

The human somatostatin receptor 3 exhibited an enhanced signaling when expressed as a fusion to the α-factor leader in the stp22 background as compared with the wild type strain. Specifically, the stp22 mutation caused an approximately two-fold increase in the levels of FUS1-lacZ induction, accompanied by a 50% decrease of $EC_{50}$ value for somatostatin-14.

Example 5
Effects of an stp22 Mutation on Signaling Through the Various GPCR

To further explore the utility of stp22 mutant strains, a comparative analysis of signaling mediated by a number of mammalian G protein-coupled receptors in the wild type and stp22 strains was conducted using ligand-spot assays. The results of this study and the above-mentioned data are summarized in Table 3.

TABLE 3

Effects of the stp22 mutation on receptor-mediated growth activation.

| Receptor | Expression vector | Growth Stimulation | |
|---|---|---|---|
| | | wild type | stp22 |
| hNocR | Cp3924 | − | + |
| Ste2-hNocr | Cp4328 | − | + |
| Inv-hNocR | Cp4735 | − | + |
| αF-hNocr | Cp4261 | + | ++ |
| hMCR4 | Cp5115 | + | +++ |
| αF-hMCR4 | Cp4421 | +++ | + |
| hMCR5 | Cp5116 | + | + |
| αF-hSSTR2 | Cp5038 | + | + |
| hSSTR2 | Cp3776 | +++ | ++++ |
| αF-hSSTR2 | Cp4698 | − | + |
| hCRFR1 | Cp5396 | + | ++ |
| hCRFR2α | Cp5394 | + | ++ |
| hBRS-3 | Cp6130 | − | + |
| hVIPR | Cp4111 | − | + |
| hCGRPR | Cp5899 | − | + |

Abbreviations: MCR, melanocortin receptor; SSTR, somatostatin receptor: NocR, nociceptin receptor; CRFR, corticotropin releasing factor receptor; αF, alpha factor leader; Ste2, Ste2 leader; Inv, invertase leader.

In most of cases, the stp22 mutation was shown to cause an increase in signaling efficiency. It should be noted, however, that the ligand-induced growth stimulation of strains expressing hMCR4, hMCR5 and hSSTR3 fused to the α-factor leader was partially or completely abolished by stp22 mutation. Typically, the α-factor leader-directed receptor expression causes stronger inhibitory effects on culture growth as compared with the expression of the native receptors. On the other hand, the stp22 mutation also causes some growth inhibition. In some cases a combination of these two negative factors may lead to a synthetic growth defect which does not allow detection of functional coupling using FUS1-HIS3 and the ligand-spot assay. Thus, if growth activation is to be used as a read-out for pheromone pathway stimulation, a leader sequence other than the α-factor leader sequence should be used. However, different results may be obtained when activation of the pheromone pathway is assessed by measurement of β-galactosidase activity using the FUS1-LacZ reporter gene. For instance, the μ-factor leader-directed expression of hSSTR3 resulted in higher FUS1-LacZ induction in a stp22 mutant than in a wild type strain (see Example 4). Thus, when a reporter gene such as FUS1-LacZ is used as a read-out, it may be suitable to still use the α-factor leader sequence with receptors that exhibit inhibitory effects on growth when the α-factor leader is used in combination with the stp22 mutation.

The fact that all the native receptors tested to date exhibited more robust signaling in stp22 background than in the wild type strains, indicates that the stp22 mutants represent a powerful tool for the development of yeast-based functional assays for G protein-coupled receptors through expression of the GPCRs in stp22 mutant strains, as described herein.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant yeast cell having an endogenous yeast pheromone system pathway which yeast cell comprises:
    (i) a heterologous G protein coupled receptor which functionally couples to the endogenous yeast pheromone system pathway; and
    (ii) a mutation which renders an endogenous yeast Stp22 protein nonfunctional.

2. The yeast cell of claim 1, which yeast cell further comprises a heterologous or chimeric G protein subunit.

3. The yeast cell of claim 1, which yeast cell further comprises a reporter gene construct which produces a detectable signal upon stimulation of the yeast pheromone system pathway.

4. The yeast cell of claim 1, which cell is a Saccharomyces cell.

5. The yeast cell of claim 1, wherein the heterologous G protein coupled receptor is a mammalian G protein coupled receptor.

6. The yeast cell of claim 5, wherein the heterologous G protein coupled receptor is a human G protein coupled receptor.

7. The yeast cell of claim 1, wherein the heterologous G protein coupled receptor is expressed in the yeast cell using a native leader sequence of the heterologous G protein coupled receptor.

8. The yeast cell of claim 1, wherein the heterologous G protein coupled receptor naturally lacks a leader sequence and is expressed in the yeast cell in its native form without a leader sequence.

9. The yeast cell of claim 1, wherein the heterologous G protein coupled receptor is expressed in the yeast cell using a yeast leader sequence.

10. The yeast cell of claim 9, wherein the yeast leader sequence is used to express a heterologous G protein coupled receptor that naturally lacks a leader sequence.

11. The yeast cell of claim 9, wherein the yeast leader sequence replaces a natural leader sequence of the heterologous G protein coupled receptor.

12. The yeast cell of claim 9, wherein the yeast leader sequence is linked to the heterologous G protein coupled receptor in addition to a natural leader sequence of the heterologous G protein coupled receptor.

13. The yeast cell of claim 9, wherein the heterologous G protein coupled receptor is expressed in the yeast cell using a yeast leader sequence other than an α-factor leader sequence.

14. The yeast cell of claim 1, wherein the heterologous G protein coupled receptor is a human nociceptin receptor.

15. The yeast cell of claim 1, wherein the heterologous G protein coupled receptor is a human melanocortin receptor.

16. The yeast cell of claim 15, wherein the human melanocortin receptor is hMCR4 or hMCR5.

17. The yeast cell of claim 1, wherein the heterologous G protein coupled receptor is a human somatostatin receptor.

18. The yeast cell of claim 17, wherein the human somatostatin receptor is hSSTR2 or hSSTR3.

19. The yeast cell of claim 1, wherein the heterologous G protein coupled receptor is a human corticotropin releasing factor receptor.

20. The yeast cell of claim 19, wherein the human corticotropin releasing factor receptor is hCRFR1 or hCRFR2α.

21. A method of identifying compounds which modulate a G protein coupled receptor, comprising the steps of:
    a) providing a yeast cell which comprise:
        (i) a heterologous G protein coupled receptor which functionally couples to the yeast pheromone system pathway; and
        (ii) a mutation which renders an endogenous yeast Stp22 protein nonfunctional;
    b) contacting the yeast cell with a compound
    c) identifying compounds which induce a change in a detectable signal in the yeast cell, wherein said detectable signal indicates that the compound is a modulator of the heterologous G protein coupled receptor.

22. The assay of claim 21, wherein the yeast cell further comprises a reporter gene construct.

23. The assay of claim 21, wherein the test compound is from a library of non-peptidic organic molecules.

* * * * *